US008808707B1

(12) United States Patent  
Siber et al.

(10) Patent No.: US 8,808,707 B1
(45) Date of Patent: Aug. 19, 2014

(54) PNEUMOCOCCAL DOSING REGIMEN

(75) Inventors: George Rainer Siber, New York, NY (US); Peter R. Paradiso, Valley Forge, PA (US); Jill G. Hackell, New City, NY (US); Stephen Paul Lockhart, Berkshire (GB); William P. Hausdorff, Saint-Lambert (BE)

(73) Assignee: Wyeth LLC, Madison, NJ (US)

( * ) Notice: Subject to any disclaimer, the term of this patent is extended or adjusted under 35 U.S.C. 154(b) by 666 days.

(21) Appl. No.: 11/740,580

(22) Filed: Apr. 26, 2007

Related U.S. Application Data

(60) Provisional application No. 60/799,053, filed on May 8, 2006.

(51) Int. Cl.
*A61K 39/385* (2006.01)
*A61K 39/02* (2006.01)
(52) U.S. Cl.
USPC ............... 424/197.11; 424/184.1; 424/193.1
(58) Field of Classification Search
None
See application file for complete search history.

(56) References Cited

U.S. PATENT DOCUMENTS

| | | | |
|---|---|---|---|
| 4,097,666 A | 6/1978 | Johnson et al. | |
| 4,673,574 A | 6/1987 | Anderson | |
| 4,686,102 A | 8/1987 | Ritchey et al. | |
| 4,902,506 A | 2/1990 | Anderson et al. | |
| 5,153,312 A | 10/1992 | Porro | |
| 5,306,492 A | 4/1994 | Porro | |
| 5,360,897 A | 11/1994 | Anderson et al. | |
| 5,614,382 A | 3/1997 | Metcalf | |
| 5,623,057 A | 4/1997 | Marburg et al. | |
| 6,224,880 B1 | 5/2001 | Chan et al. | |
| 6,248,570 B1 | 6/2001 | Michon et al. | |
| 6,620,928 B2 | 9/2003 | Besemer | |
| 7,018,637 B2 | 3/2006 | Chong et al. | |
| 7,384,775 B2 | 6/2008 | Zagursky et al. | |
| 7,582,459 B2 | 9/2009 | Hamidi et al. | |
| 7,588,765 B2 | 9/2009 | Porro | |
| 7,935,787 B2 | 5/2011 | Khandke et al. | |
| 2001/0048929 A1 | 12/2001 | Chong et al. | |
| 2003/0147922 A1* | 8/2003 | Capiau et al. | 424/244.1 |
| 2003/0180316 A1 | 9/2003 | Boutriau et al. | |
| 2004/0096461 A1 | 5/2004 | Michon et al. | |
| 2004/0202668 A1* | 10/2004 | Boutriau et al. | 424/184.1 |
| 2004/0213817 A1 | 10/2004 | Miller et al. | |
| 2006/0165730 A1 | 7/2006 | Porro | |
| 2006/0228380 A1 | 10/2006 | Hausdorff et al. | |
| 2007/0110762 A1 | 5/2007 | Jessouroun et al. | |
| 2007/0184071 A1 | 8/2007 | Hausdorff et al. | |
| 2007/0231340 A1 | 10/2007 | Hausdorff et al. | |
| 2009/0130137 A1 | 5/2009 | Hausdorff et al. | |
| 2011/0071279 A1 | 3/2011 | Hausdorff et al. | |

FOREIGN PATENT DOCUMENTS

| | | |
|---|---|---|
| EP | 497524 B1 | 7/1998 |
| EP | 497525 B1 | 8/1998 |
| WO | 9851339 A1 | 11/1998 |
| WO | 00/56358 A2 | 9/2000 |
| WO | 0056359 A2 | 9/2000 |
| WO | 0062801 A2 | 10/2000 |
| WO | 02/00249 A2 | 1/2002 |
| WO | 0222167 A2 | 3/2002 |
| WO | WO 02/053761 A2 | 7/2002 |
| WO | 03051392 A2 | 6/2003 |
| WO | WO 03/051392 * | 6/2003 |
| WO | 2004067574 A2 | 8/2004 |

OTHER PUBLICATIONS

Powers et al 1995 Journal of Infectious Diseases vol. 173 pp. 1014-1018.*
Mufson et al 1991 Vaccine vol. 9 pp. 403-407.*
Fedson et al., *Pneumococcal Vaccine After 15 Years of Use.* Arch. Intern. Med., 154: 2531-2535, 1994.
French, N., *Use of Pneumococcal Polysaccharide Vaccines: No Simple Answers.* J. Infect., 46: 78-86, 2003.
Fine, M.J., et al., *Efficacy of Pneumococcal Vaccination in Adults: A Meta-analysis of Randomized Controlled Trials.* Arch. Int. Med. 154: 2666-2677, 1994.
Moore, R.A., *Are the pneumococcal polysaccharide vaccines effective? Meta-analysis of the prospective trials.* BMC Fam. Prac. 1: 1-10, 2000.
Conaty, S., et al., *The effectiveness of pneumococcal polysaccharaide vaccines in adults: a systematic review of observational studies and comparison with results from randomized controlled trials.* Vaccine 22: 3214-3224, 2004.
Jackson, L.A., et al., *Effectiveness of Pneumococcal Polysaccharide Vaccine in Older Adults.* N. Engl. J. Med. 348: 1747-1755, 2003.
Davidson, M., et al., *Immunogenicity of Pneumococcal Revaccination in Patients With Chronic Disease.* Arch. Intern Med. 154: 2209-2214, 1994.
Rodriguez-Barradas M.C., *IgG Antibody to Pneumococcal Capslar Polysaccharide in Human Immunodeficiency Virus-Infected Subjects: Persistence of Antibody in Responders, Revaccination in Nonresponders, and Relationship of Immunoglobulin Allotype to Response.* J. Infect. Dis. 173: 1347-1353, 1996.

(Continued)

*Primary Examiner* — Padma V Baskar

(74) *Attorney, Agent, or Firm* — Victoria S. Molenda

(57) ABSTRACT

Methods of immunizing older adult subjects against *Streptococcus pneumoniae* infection are provided. Provided methods comprise immunization of naïve adult subjects with a conjugated pneumococcal polysaccharide vaccine. Optionally, initial immunization may be followed by additional immunization doses comprising conjugated pneumococcal polysaccharide vaccine or unconjugated pneumococcal polysaccharide vaccine composition.

36 Claims, No Drawings

(56) References Cited

OTHER PUBLICATIONS

Rubins, J.B., *Magnitude, Duration, Quality, and Function of Pneumococcal Vaccine Responses in Elderly Adults.* J. Infect. Dis. 178: 431-440, 1998.

Sankilampi, U., *Response to Hepatitis A Vaccination in Human Immunodeficiency Virus-Infected and—Uninfected Homosexual Men.* J. Infect. Dis. 176: 1100-1104, 1997.

Artz et al., *Pneumococcal Vaccination and Revaccination of Older Adults.* Clin. Microbiol. Rev. 16: 308-318, 2003.

Mufson, M.A., et al., *Revaccination with pneumococcal vaccine of elderly persons 6 years after primary vaccination.* Vaccine 9: 403-407, 1991.

Borgondo, J.M., et al., *Vaccination and Revaccination with Polyvalent Pneumococcal Polysaccharide Vaccines in Adults and Infants.* Proc. Soc. Exp. Biol. Med. 157: 148-154, 1978.

Linnemann, G.C., et al., *Revaccination of Renal Transplant and Hemodialysis Recipients With Pneumococcal Vaccine.* Arch Intern. Med. 146: 1554-1556, 1996.

Huebner, R., et al., Ped. Inf. Dis. J., 21:1004-1007, 2002.

S. Black, et al, Safety and efficacy of the seven-valent pneumococcal conjugate vaccine: evidence from Northern California. *Eur J Pediatr.* 161 Suppl 2:S127-31, 2002.

K. Klugman, et al, *A Trial of a 9-Valent Pneumococcal Conjugate Vaccine in Children with and Those without HIV Infection.* N. Engl J Med. 349:1341-8, 2003.

F. Cutts, et al, *Efficacy of nine-valent pneumococcal conjugate vaccine against pneumonia and invasive pneumococcal disease in The Gambia: randomised, double-bind, placebo-controlled trial.* Lancet 365:1139-46, 2005.

O'Brien, K.L., et al., "Combined schedules of pneumococcal conjugate and polysaccharide vaccines: is hyporesponsiveness an issue?", Lancet Infect Dis 7(9):597-606 (2007).

Torling, J., et al., "Revaccination with the 23-valent pneumococcal polysaccharide vaccine in middle-aged and elderly persons previously treated for pneumonia," Vaccine 22:96-103 (2003).

Ada, C. et al., "Arbohydrate-protein conjugate vaccines", Clinical Microbiology Infection, 9(2):79-85 (2003).

Black, S.B., et al., "Postlicensure evaluation of the effectiveness of seven valent pneumococcal conjugate vaccine", Pediatric Infectious Disease Journal, 20(12):1105-1107 (2001).

Block, S.L. et al., "Pneumococcal serotypes from acute otitis media in rural Kentucky", Pediatric Infectious Disease Journal, 21(9) 859-865 (2002).

Buckingham, S.C., et al., "Incidence and etiologies of complicated parapneumonic effusions in children, 1996 to 2001", Pediatric Infectious Disease Journal, 22(6):499-596 (2003).

Butler, J.C., et al., "Serotype Distribution of *Streptococcus pneumoniae* Infections among Preschool Children in the United Slates, 1978-1994: Implications for Development of a Conjugate Vaccine", Journal of Infectious Diseases, 171 (4):885-889 (1995).

Hausdorff, W.P.; et al., "Which Pneumococcal Serogroups Cause the Most Invasive Disease: Implications for Conjugate Vaccine Formulation and Use, Part 1", Clinical Infectious Diseases, 30(1):100-121 (2000).

Hausdorff, W.P., et al. "The contribution of specific pneumococcal serogroups to different disease manifestations: implications for conjugate vaccine formulation and use, part II", Clinical Infectious Diseases, 30(1):122-140 (2000).

Hausdorff, W.P. et al., "Invasive pneumococcal disease in children: geographic and temporal variations in incidence and serotype distribution", European Journal of Pediatrics, 161(Suppl. 2):S135-139 (2002).

Hausdorff, W.P., et al., "Epidemiological differences among pneumococcal serotypes", Lancet Infectious Diseases, 5(2):83-93,(2005).

Hausdorff, W.P., et al., "Geographical differences in invasive pneumococcal disease rates and serotype frequency in young children", Lancet, 357(9260):950-952 (2001).

Hausdorff, W.P., et al., "Multinational study of pneumococcal serotypes causing acute otitis media in children", Pediatric Infectious Disease Journal, 21(11):1008-1016 (2002).

Hofmann J., et al., "The prevalence of drug-resistant *Streptococcus pneumoniae* in Atlanta " New England Journal of Medicine, 333(8):481-486 (1995).

Joloba, M.L., et al., "Pneumococcal Conjugate Vaccine Serotypes of *Streptococcus pneumoniae* Isolates and the Antimicrobial Susceptibility of Such Isolates in Children with Otitis Media", Clinical Infectious Diseases, 33 (9):1469-1494 (2001).

Klein, D.L., et al., "Development and testing of *Streptococcus pneumoniae* conjugate vaccines", Clinical Microbiology and Infection, 5(4):4S17-4S28 (1999).

Klein, D.L., "Pneumococcal Conjugate Vaccines: Review and Update," Microbial Drug Resistance, 1(1):49-58 (1995).

O'Brien, K.L., et al., "Efficacy and safety of seven-valent conjugate pneumococcal vaccine in American Indian children: group randomised trial", Lancet, 362(9381).355-361 (2003).

O'Brien, K.L., et al., "Potential Impact of Conjugate Pneumococcal Vaccines on Pediatric Pneumococcal Diseases", American Journal of Epidemiology, 159(7):634-644 (2004).

Penn, R.L., et al., "Antibody responses in adult volunteers to pneumococcal polysaccharide types 19F and 19A administered singly and in combination", Infection and Immunity, 36(3):1261-1262 (1982).

Robbins, J.B., et al., "Considerations for Formulating the Second-Generation Pneurnococcal Capsular Polysaccharide Vaccine with Emphasis on the Cross-Reactive Types Within Groups", Journal of Infectious Diseases, 148(6)1136-1159 (1983).

Robinson, K.A., et al., "Epidemiology of Invasive *Streptococcus pneumoniae* Infections in the United States, 1995-1998", JAMA, 285(13):1729-1735 (2001).

Rudolph, K.M., et al. "Serotype Distribution and Antimicrobial Resistance Patterns of Invasive Isolates of *Streptococcus pneumoniae* : Alaska, 1991-1998", Journal of Infectious Diseases, 182(2)490-496 (2000).

Sniadack, D.H., et al., "Potential interventions for the prevention of childhood pneumonia: geographic and temporal differences in serotype and serogroup distribution of sterile site pneumococcal isolates from children-implications for vaccine strategies", Pediatric Infectious Disease Journal, 14(6)503-510 (1995).

Whitney, C.G., et al., "Increasing prevalence of multidrug-resistant *Streptococcus pneumoniae* in the United States", New England Journal of Medicine, 343(26):1917-1924 (2000).

Whitney, C.G. et al., "Decline in Invasive Pneumococcal Disease after the Introduction of Protein-Polysaccharide Conjugate Vaccine", New England Journal of Medicine, 348(18):1737-1746 (2003).

De La Pena, C., et al., "Present and future of the pneumonia vaccination", Pediatrika, 24(4):147-155 (2004).

Overturf, G.D., "Pneumococcal Vaccination in Children", Seminars in Pediatric Infectious Diseases, 13(3):155-164 (2002).

Panacea Biotec Ltd., "Opposition of the Grant of Patent", Indian Patent Application No. 8081/DELNP/2007, 29 pages, dated Aug. 26, 2010.

Wyeth LLC, "Reply Statement of the Applicant", Indian Patent Application No. 8081/DELNP/2007, 34 pages, dated Sep. 17, 2013.

EMEA, Public Statement: Prevenar—Shortage of Supply, 2 pages, Mar. 22, 2004, available at http://www.ema.europa.eu/docs/en_GB/document_library/Public_statement/2009/12/WC500017611.pdf.

European Patent Office, "Summons to Attend Oral Proceedings", Opposition to European Patent No. EP1868645, 13 pages, mailed Jan. 31, 2014.

SK Chemicals Co., Ltd, "Brier", Invalidation Grounds Against Korean Patent No. 1298053, 28 pages, dated Jan. 3, 2014 (English Translation only).

Sankilampi, U., et al., "Persistence of Antibodies to Pneumococcal Capsular Polysaccharide Vaccine in the Elderly", The Journal of Infectious Diseases, 176(4):1100-1104 (1997).

Neilsen, G.A., et al., "Response to Hepatitis A Vaccination in Human Immunodeficiency Virus-Infected and Uninfected Homosexual Men", J. Infect, Dis., 176:1084-1067 (1997).

(56) References Cited

OTHER PUBLICATIONS

Wyeth LLC, "Patentee's Response to Notices of Opposition in European Patent No. EP1868645 (Application No. 2 06740419.4)", 31 pages, submitted Aug. 2, 2013.

Romero-Steiner, S., et al., "Reduction in Functional Antibody Activity Against *Streptococcus pneumoniae* in Vaccinated Elderly Individuals Highly Correlates with Decreased IgG Antibody Avidity", Clinical Infectious Diseases, 29:281-288 (1999).

Janoff, E.N., et al., "Editorial Response: Predicting Protection Against Encapsulated Pathogens", Clinical Infectious Diseases, 29:289-291 (1999).

Merck & Co., Inc., "European Patent 1 868 645 in the name of Wyeth LLC Opposed by Merck & Co., Inc.", 11 pages, submitted Dec. 4, 2012.

Strawman Limited, "Opposition Against EP-B1 1868 645", 25 pages, submitted Dec. 6, 2012.

Zimmer, F.J., "Opposition against European Patent No. 1 868 645 (EP 06 740 419.4)", 19 pages, submitted Dec. 6, 2012.

Crucell Holland B.V., "Opposition by Crucell Holland B.V. Against the Grant of EP 1 868 645 B1 in the name of Wyeth LLC", 18 pages, submitted Dec. 7, 2012.

Novartis Vaicines And Diagnostics S.R.L., "European Patent 1868645, Wyeth LLC, Arguments in Support of Opposition", 16 pages, submitted Dec. 7, 2012.

Andrews, C.P., et al., "Safety and Immunogenicity of 15-valent Pneumococcal Conjugate Vaccine (PCV15) Compared to PCV13 in Healthy Older Adults", 9th International Symposium on Pneumococci and Pneumococcal Diseases (Hyderabad, India), Abstract O-010 & poster (Mar. 9-13, 2014).

Bonten, M., et al., "Community Acquired Pneumonia Immunisation Trial in Adults (CAPITA)", 9th International Symposium on Pneumococci and Pneumococcal Diseases (Hyderabad, India), Abstract O-015 (Mar. 9-13, 2014).

Greenberg, D., et al., "Safety and Immunogenicity of 15-valent Pneumococcal Conjugate Vaccine (PCV-15) Compared to PCV-13 in Healthy Infants" [Abstract ISPPD-0197], Pneumonia, 3:99 (2014).

Horn, M., et al., "Safety and Immunogenicity of an Investigational 12-valent Pneumococcal Non-typeable Haemophilus influenzae Protein D Conjugate Vaccine in Toddlers: Phase I Study", 9th International Symposium on Pneumococci and Pneumococcal Diseases (Hyderabad, India), Abstract P-186 & poster (Mar. 9-13, 2014).

Kim, L., et al., "Impact of 13-valent Pneumococcal Conjugate Vaccine (PCV13) on Invasive Pneumococcal Disease (IPD) Among Adults in the U.S.", 9th International Symposium on Pneumococci and Pneumococcal Diseases (Hyderabad, India), Abstract P-293 (Mar. 9-13, 2014).

Martinez, A.C. et al., "Immunogenicity and Safety of 11- and 12-valent Pneumococcal Non-typeable Haemophilus influenzae Protein D-Conjugate Vaccines (11VPHID-CV, 12VPHID-CV) in Infants: Phase II Study", 9th International Symposium on Pneumococci and Pneumococcal Diseases (Hyderabad, India), Abstract P-196 & poster (Mar. 9-13, 2014).

Wyeth LLC, "Response", Case No. 2013 Dang 2673 (Invalidation Action Against Korean Patent No. 1298053), 21 pages, submitted May 7, 2014 (English Translation Only).

Wyeth LLC, "Request for Correction of Korean Patent No. 1298053", 7 pages, submitted May 7, 2014 (English Translation Only).

Wyeth LLC, "Response to First Examination Report", Indian Patent Application No. 8081/DELNP12007, 29 pages, submitted Jun 17, 2014.

* cited by examiner

PNEUMOCOCCAL DOSING REGIMEN

PRIORITY INFORMATION

The present application claims priority to provisional patent application U.S. Ser. No. 60/799,053 filed on May 8, 2006. The entire contents of this provisional patent application are incorporated herein by reference.

BACKGROUND OF THE INVENTION

*Streptococcus pneumoniae* is a bacterial pathogen implicated in many respiratory and systemic infections, including pneumonia, meningitis, otitis media, bacteremia, sinusitis, peritonitis, and arthritis. Infection with *S. pneumoniae* can be fatal; other serious results of infection can include neurological effects (e.g., learning disabilities, seen in meningitis patients) or hearing loss (in recurrent otitis media infections). Young children and the elderly are at a particularly high risk for infection with *S. pneumoniae*, as are immuno-compromised populations and members of certain ethnic groups.

Historically, antimicrobial therapies have been useful in reducing morbidity and mortality rates associated with invasive pneumococcal disease; however, the increasing prevalence of multi-drug resistant strains of *S. pneumoniae* poses troubling difficulties for attempts to control infections through drug therapy alone.

Vaccination efforts have recently proven effective in reduction of incidence of *S. pneumoniae* infection rates. Current vaccines contain polysaccharide molecules from the capsule of different serotypes of *S. pneumoniae*; more than 90 different serotypes have been identified. with different incidences worldwide. Some vaccines, known as "unconjugated" vaccines, contain free polysaccharides. More recently, "conjugated" vaccines, in which saccharide molecules are linked to a peptide carrier, have been developed. An unconjugated vaccine containing polysaccharides from 23 different pneumococcal serotypes has been licensed for use in children over 2 years of age; a conjugate vaccine containing 7 different polysaccharide valencies has been licensed for pediatric use. Introduction and use of this 7-valent conjugate vaccine, PRE-VNAR® (pneumococcal 7-valent conjugate vaccine [diphtheria $CRM_{197}$ protein]. produced by Wyeth Pharmaceuticals, Inc. of Philadelphia, Pa. and containing polysaccharides from serotypes 4, 6B. 9V, 14, 18C, 19F, and 23F conjugated to the Diphtheria $CRM_{197}$ protein), in the United States has reduced the incidence of invasive pneumococcal disease (IPD) in children nearly 94% (from 80 per 100,000 in 1998-1999 to 4.6 per 100,000 in 2003).

While young children are among those most at risk for *S. pneumoniae* infections, disproportionate morbidity and mortality result from invasive pneumococcal disease occurring in older adults. The incidence of invasive pneumococcal infection begins to increase at about age 50 years and increases sharply at age 65 years. *S. pneumoniae* is the most common cause of community-acquired pneumonia in the United States, resulting in hospitalizations and deaths in persons over 65 years (Robinson, K. A. et al., *JAMA* 285: 1729-35, 2001). Deaths occur in approximately 14% of patients hospitalized with invasive disease. Persons living in long term care facilities remain a particularly susceptible population for invasive pneumococcal disease as compared to similar older persons living in community settings (Kupronia, B. A., et al., *JAGS* 51: 1520-1525, 2003).

The only currently licensed pneumococcal vaccine for use in adult populations is the 23 valent unconjugated polysaccharide vaccine. Although this vaccine has been recommended by the CDC Advisory Committee on Immunization Practices (ACIP) Guidelines for prevention of pneumococcal disease in persons 65 years of age or older, significant controversy exists relating to its efficacy. Specifically, wide variation in clinical efficacy has been observed in with this vaccine, which may be related, for example, to age, or disease manifestation (see, e.g., Fedson et al., Arch. Intern. Med., 154: 2531-2535, 1994; and French J. Infect., 46: 78-86, 2003). The vaccine appears to be particularly ineffective in protecting the elderly against pneumococcal pneumonia, and also in protecting any population against otitis media infections. Additionally, meta-analyses of randomized controlled studies have not found a clear protective effect for pneumococcal pneumonia in high-risk groups such as elderly populations (See, e.g., Fine, M. J., et al., *Arch. Int. Med.* 154: 2666-2677, 1994; Moore, R. A., *BMC Fam. Prac.* 1:1-10, 2000; Conaty, S., et al., *Vaccine* 22: 3214-3224, 2004; and Jackson, L. A., et al., *N. Engl. J. Med.* 348: 1747-1755, 2003. Furthermore, analyses of immuno-protective effects and duration of response have suggested populations such as the older populations and immuno-compromised patients may generate only limited immune response following polysaccharide vaccination, and resulting antibody concentrations may decrease rapidly subsequent to vaccination (See, e.g., Davidson, M., et al., *Arch. Intern Med.* 154: 2209-2214, 1994; Rodriguez-Barradas M. C., *J. Infect. Dis.* 173: 1347-1353, 1996; Rubins, J. B., *J. Infect. Dis.* 178: 431-440, 1998; and Sankilampi, U., *J. Infect. Dis.* 176: 1100-1104, 1997. Moreover, once a subject has been initially vaccinated with the unconjugated polysaccharide vaccine, revaccination has been found to result in subsequent hyporesponsiveness. (See, e.g., Artz et al., *Clin. Microbiol. Rev.* 16: 308-318, 2003; Mufson, M. A., et al., *Vaccine* 9: 403-407, 1991; Borgondo, J. M., et al., *Proc. Soc. Exp. Biol. Med.* 157: 148-154, 1978; and Linnemann, G. C., et al., *Arch Intern. Med.* 146: 1554-1556, 1996.

There remains a need for improved strategies for protecting high risk populations, and particularly older and elderly populations, from infections with *S. pneumoniae*.

SUMMARY OF THE INVENTION

The present invention encompasses the finding that an initial immunization of naïve (previously un-immunized) older subjects with pneumococcal conjugate vaccine results in generation of an improved immunoprotective response over presently available vaccination. Still further, the invention encompasses the finding that an initial immunization dose with conjugate vaccine followed by at least one additional immunization dose with either conjugate or unconjugated polysaccharide vaccine gives a beneficial immunoprotective effect. Thus, provided are methods of immunizing (and re-immunizing) older adult subjects against pneumococcal infection. Provided methods include methods for production of antibody titer in naïve adults by immunizing adults with a conjugated pneumococcal polysaccharide vaccine. Alternatively or additionally, provided methods further comprise repeat dosing immunization schedules wherein antibody titers are produced that exceed levels and functional activity of those observed in prior methods and studies utilizing pneumococcal polysaccharide vaccines.

DETAILED DESCRIPTION OF CERTAIN PREFERRED EMBODIMENTS OF THE INVENTION

The invention relates to the ability of pneumococcal conjugate vaccines to increase immunoprotective response generated in older vaccination subjects, as compared to currently available vaccination approaches. For the purposes of this invention, "pneumococcus" or "pneumococcal" refers to *Streptococcus pneumoniae*. "Pneumococcal disease" refers to disease caused by *Streptococcus pneumoniae* infection. As described herein, pneumococcal conjugate vaccines are useful in methods of vaccination of older subjects against *Streptococcus pneumoniae* infection and/or disease. The invention relates to methods of eliciting immunoprotective response against *S. pneumoniae* infection in older subjects, including elderly subjects. Further, the invention relates to methods of administering additional dose(s) of pneumococcal vaccine to an older subject in order to extend immunoprotection against *S. pneumoniae* infection.

The present invention provides improved methods of vaccination for prevention or amelioration of pneumococcal infection of older populations, including elderly persons. In the context of the invention a human subject is considered an older subject if s/he is 50 years or over in age. A subject is considered elderly if s/he is 60 years or over in age, typically over 65.

Pneumococcal Vaccines

*S. Pneumoniae* Polysaccharide Antigens

There are at least 90 sub-types of the gram positive *S. pneumoniae* organism, each having a different chemical structure of capsular polysaccharide. The capsular polysaccharide is the principal virulence factor of the pneumococcus. It is these capsular polysaccharides which, when isolated, are useful for human induction of antibody response and effective vaccine generation. Each of the serotype designation as used herein are designated according to the Danish nomenclature Typically the *Streptococcus pneumoniae* vaccine used in the methods of the present invention comprises polysaccharide antigens (unconjugated or conjugated to a polypeptide carrier) derived from at least four pneumococcus serotypes. For example, a vaccine useful in the provided methods may include at least one polysaccharide selected from serotypes 6B, 14, 19F and 23F. In some embodiments, a vaccine comprises at least two or three polysaccharide selected from serotypes 6B, 14, 19F and 23F. In still other embodiments, all four polysaccharide selected of serotypes 6B, 14, 19F and 23F are included in a vaccine of use in the present invention.

In some embodiments, a vaccine useful in the provided methods may include at least one polysaccharide selected from serotypes 4, 6B, 9V, 14, 18C, 19F, and 23F. In some embodiments, a vaccine comprises at least two, at least three or at least four polysaccharides selected from serotypes 4, 6B, 9V, 14, 18C, 19F, and 23F. In still other embodiments, a vaccine comprises at least five, or at least six polysaccharides selected from serotypes 4, 6B, 9V, 14, 18C, 19F, and 23F. In certain embodiments, all seven polysaccharides of serotypes 4, 6B, 9V, 14, 18C, 19F, and 23F are included in a vaccine used in the provided methods.

In some embodiments, a vaccine useful in the provided methods may include at least one polysaccharide selected from serotypes 1, 4, 5, 6B, 9V, 14, 18C, 19F, and 23F. In some embodiments, a vaccine comprises at least two, at least three, at least four, or at least five polysaccharides selected from serotypes 1, 4, 5, 6B, 9V, 14, 18C, 19F, and 23F. In still other embodiments, a vaccine comprises at least six, at least seven, or at least eight polysaccharides selected from serotypes 1, 4, 5, 6B, 9V, 14, 18C, 19F, and 23F are included in a vaccine used in the provided methods. In certain embodiments, all nine polysaccharides of serotypes 1, 4, 5, 6B, 9V, 14, 18C, 19F, and 23F are included in a vaccine used in the provided methods.

In still additional embodiments, a vaccine useful in the methods of the invention comprises at least one, polysaccharide selected from serotypes 1, 4, 5, 6B, 7F, 9V, 14, 18C, 19F, and 23F. In some embodiments, a vaccine comprises at least two or at least three polysaccharides selected from serotypes 1, 4, 5, 6B, 7F, 9V, 14, 18C, 19F and 23F. In other embodiments, a vaccine comprise at least four, at least five, or at least six polysaccharides selected from serotypes 1, 4, 5, 6B, 7F, 9V, 14, 18C, 19F and 23F. In still other embodiments, at least seven, at least eight, or at least nine, polysaccharides are included in a vaccine which are selected from serotypes 1, 4, 5, 6B, 7F, 9V, 14, 18C, 19F and 23F. In certain embodiments, all ten polysaccharides of serotypes 1, 4, 5, 6B, 7F, 9V, 14, 18C, 19F and 23F are included in a vaccine used in the provided methods.

In still additional embodiments, a vaccine useful in the methods of the invention comprises at least one, polysaccharide selected from serotypes 1, 3, 4, 5, 6B, 7F, 9V, 14, 18C, 19F, and 23F. In some embodiments, a vaccine comprises at least two or at least three polysaccharides selected from serotypes 1, 3, 4, 5, 6B, 7F, 9V, 14, 18C, 19F and 23F. In other embodiments, a vaccine comprise at least four, at least five, or at least six polysaccharides selected from serotypes 1, 3, 4, 5, 6B, 7F, 9V, 14, 18C, 19F and 23F. In still other embodiments, at least seven, at least eight, at least nine, or at least ten, polysaccharides are included in a vaccine which are selected from serotypes 1, 3, 4, 5, 6B, 7F, 9V, 14, 18C, 19F and 23F. In certain embodiments, all eleven polysaccharides derived from serotypes 1, 3, 4, 5, 6B, 7F, 9V, 14, 18C, 19F and 23F are included in a vaccine used in the provided methods.

In still additional embodiments, a vaccine useful in the methods of the invention comprises at least one polysaccharide selected from serotypes 1, 3, 4, 5, 6A, 6B, 7F, 9V, 14, 18C, 19A, 19F, and 23F. In some embodiments, a vaccine comprises at least two, at least three or at least four polysaccharides selected from serotypes 1, 3, 4, 5, 6A, 6B, 7F, 9V, 14, 18C, 19A, 19F and 23F. In other embodiments, a vaccine comprise at least five, at least six, at least seven, or at least eight polysaccharides selected from serotypes 1, 3, 4, 5, 6A, 6B, 7F, 9V, 14, 18C, 19A, 19F and 23F. In still other embodiments, at least nine, at least eight, at least ten, at least eleven, or at least twelve polysaccharides are included in a vaccine which are selected from serotypes 1, 3, 4, 5, 6A, 6B, 7F, 9V, 14, 18C, 19A, 19F and 23F. In certain embodiments, all thirteen polysaccharides derived from serotypes 1, 3, 4, 5, 6A, 6B, 7F, 9V, 14, 18C, 19A, 19F and 23F are included in a vaccine used in the provided methods.

In still further embodiments, a vaccine useful in the methods of the invention comprises at least one, at least two, at least three, at least four, or at least five polysaccharides selected from serotypes 1, 2, 3, 4, 5, 6A, 6B, 7F, 8, 9N, 9V, 10A, 11A, 12F, 14, 15B, 17F, 18C, 19A, 19F, 20, 22F, 23F and 33F. In other embodiments, a vaccine comprise at least six, at least seven, at least eight, at least nine, or at least ten polysaccharides selected from serotypes 1, 2, 3, 4, 5, 6A, 6B, 7F, 8, 9N, 9V, 10A, 11A, 12F, 14, 15B, 17F, 18C, 19A, 19F, 20, 22F, 23F and 33F. In still other embodiments, at least seven, at least eleven, at least twelve, at least thirteen, at least fourteen, or at least fifteen, polysaccharides are included in a vaccine which are selected from serotypes 1, 2, 3, 4, 5, 6A, 6B, 7F, 8, 9N, 9V, 10A, 11A, 12F, 14, 15B, 17F, 18C, 19A, 19F, 20, 22F, 23F and 33F. In still other embodiments, at least sixteen, at least seventeen, at least eighteen, at least nineteen, or at least twenty, polysaccharides are included in a vaccine which are selected from serotypes 1, 2, 3, 4, 5, 6A, 6B, 7F, 8, 9N, 9V, 10A, 11A, 12F, 14, 15B, 17F, 18C, 19A, 19F, 20, 22F, 23F and 33F. In certain embodiments, a vaccine comprises at least twenty one, at least twenty two, or at least twenty three polysaccharides derived from serotypes 1, 2, 3, 4, 5, 6A, 6B, 7F, 8, 9N, 9V, 10A, 11A, 12F, 14, 15B, 17F, 18C, 19A, 19F, 20, 22F, 23F and 33F. In yet another embodiment, the invention method contemplates use of vaccine comprising at least 23 polysaccharide antigens derived of serotypes 1, 2, 3, 4, 5, 6A, 6B, 7F, 8, 9N, 9V, 10A, 11A, 12F, 14, 15B, 17F, 18C, 19A, 19F, 20, 22F, 23F and 33F. In certain embodiments, the invention method contemplates use of vaccine comprising all 23 polysaccharide antigens derived of serotypes 1, 2, 3, 4, 5, 6B, 7F, 8, 9N, 9V, 10A, 11A, 12F, 14, 15B, 17F, 18C, 19A, 19F, 20, 22F, 23F and 33F.

Although the above polysaccharides may be used in their full-length, native form, it should be understood that size-reduced polysaccharides may also be used which are still immunogenic (see for example EP 497524 and 497525).

Polysaccharide Vaccines

As discussed above, isolated capsular polysaccharides are useful vaccine antigens. Multiple type specific capsular polysaccharides have been prepared individually, and combined for generation of a vaccine which is capable of eliciting an immune response against multiple pneumococcal strains. Such vaccine generations are well known as unconjugated pneumococcal polysaccharide vaccine preparations. Two different unconjugated pneumococcal vaccines have been reported and approved for administration to humans. The first unconjugated polysaccharide pneumococcal vaccine comprised a 14-valent unconjugated pneumococcal polysaccharide vaccine; the second, currently in use, was a 23-valent unconjugated pneumococcal polysaccharide vaccine.

The currently available 23 valent polysaccharide vaccine includes polysaccharide from the following serotypes: 1, 2, 3, 4, 5, 6B, 7F, 8, 9N, 9V, 10A, 11A, 12F, 14, 15B, 17F, 18C, 19F, 19A, 20, 22F, 23F and 33F, accounting for about 90% of pneumococcal blood isolates presently identified as relevant for infection. In principle, a polysaccharide vaccine could be modified so as to include additional and/or different combinations of serotype specific polysaccharides. Modification and/or addition of polysaccharides may be desirable for example, as infectious serotypes may shift over time, and/or various serotypes may be particularly relevant for specific populations.

Currently, the 23-polyvalent polysaccharide vaccine (such as PNEUMOVAX® 23 (pneumococcal vaccine polyvalent), Merck, Whitehouse Station, N.J., also PNEUMOVAX® II (pneumococcal vaccine polyvalent), Aventis Pasteur MSD, Berkshire, UK) is available for adults and children over two years of age. Each recommended dose of vaccine (0.5 ml) contains 25 µg of each of 23 type-specific polysaccharides dissolved in isotonic saline. The vaccine is often generally referred to as 23vPS vaccine or 23vPS to reflect 23 valence and free polysaccharide (PS). PNEUMOVAX® 123 (pneumococcal vaccine polyvalent) is described at pages 1768-1770 of the 1997 edition of the Physician's Desk Reference (Medical Economics, Montvale, N.J.). PNEUMOVAX® 23 (pneumococcal vaccine polyvalent) is prepared by a process that involves purifying the above described 23 polysaccharides from S. pneumoniae, followed by dissolving the purified polysaccharides in isotonic saline containing 0.25% phenol as a preservative. The 23-valent polysaccharide vaccine, and production of the saccharides is described in U.S. Pat. No. 4,686,102.

In general, a variety of methods for preparing unconjugated pneumococcal polysaccharide vaccines suitable for use in the present invention are known in the art. In many cases, polysaccharides are purified individually from S. pneumoniae serotypes. In general, a starting point in the entire process of making the vaccine is the purification of bacterial capsular polysaccharides from a fermentation broth of a particular serotype of S. pneumoniae. Alternatively or additionally, polysaccharides may be isolated simultaneously from more than one S. pneumoniae serotype, so that a mixture of serotype polysaccharides is obtained and the relevant serotype polysaccharides are already combined. In some instances, different polysaccharides may require sufficiently different isolation procedures that such simultaneous isolation is not desirable or is not feasible. Methods of purifying polysaccharides from S. pneumoniae are well known. For example, a purification process for the polysaccharides is described in U.S. Pat. Nos. 4,686,102; 4,242,501; 4,221,906; 5,623,057; and 5,847,112. Preparation of the 23-valent polysaccharides has been described in U.S. Pat. No. 4,686, 102.

Alternatively, pneumococcal polysaccharides are also commercially available (e.g., available from ATCC), and may be used as starting material for vaccine preparation. Individual native polysaccharides (in a powder form) are dissolved in water, and incubated with a salt (e.g., sodium chloride) to dissociate residual impurities which are then removed by filtration. Purified polysaccharides can then be dissolved in an appropriate solvent or buffer (e.g., isotonic saline), optionally containing a preservative (e.g., 0.25% phenol).

Resulting purified polysaccharides can then be used, either individually, or in combination for production of a vaccine. Methods of preparation of unconjugated vaccines that are suitable for use in the present invention are described in, e.g., U.S. Pat. Nos. 4,242,501, 4,221,906 and 4,686,102, and European Patent Application EP 0 002 404. Preparation of the 23-valent polysaccharides has been described in U.S. Pat. No. 4,686,102.

Conjugate Vaccines

Conjugate vaccines are prepared by linking isolated or purified polysaccharides with a polypeptide carrier. It is generally believed that conjugate vaccines promote stronger T-cell-dependent immune responses than do unconjugated polysaccharides. In particular, conjugate vaccines have proven to be more strongly immunogenic in children under two years of age; such young children do not mount a strong response to most unconjugated polysaccharides.

In general, any polypeptide carrier can be used that allows coupling of polysaccharide antigens so that they are displayed in a way that induces an immunoprotective immune response. More than one polysaccharide antigen may be coupled to the same polypeptide carrier molecule or entity. For instance, two or more different polysaccharide antigens (whether first isolated separately and then combined or isolated together) may be simultaneously coupled to polypeptide carrier in the same reaction. Or, a polypeptide carrier that has already been coupled with one polysaccharide antigen can subsequently be coupled with another. In other embodiments, individual polypeptide carrier molecules or entities are each coupled to only one polysaccharide antigen. For example, individual isolated antigens may be separately coupled to polypeptide carriers and then combined with one another after coupling. All polysaccharide antigens in a particular conjugate vaccine may be coupled to the same polypeptide carrier, or alternatively different polypeptide carriers may be employed.

Polypeptide Carriers

In many embodiments of the invention, conjugate vaccines will comprise polysaccharide antigens coupled to one or more polypeptide carriers. In principle, any polypeptide suitable for presenting pneumococcal polysaccharide antigens such that an immunoprotective immune response to the polysaccharide antigen is induced may be utilized in accordance with the present invention.

A polypeptide carrier can be used, In general a polypeptide carrier may have at least about 50 amino acid residues in the chain, preferably 100-1000 amino acid residues. In certain instances, it may be desirable that the polypeptide carrier have at least some lysine residues or glutamate or aspartate residues of the amino acids sequence. The pendant amines of lysine residues and pendant carboxylates of glutamine and aspartate are convenient for attaching an agent (e.g., polysaccharide).

Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier and conjugate. Additionally suitable polypeptide carriers include bacterial toxins, toxoids, or inactivated toxin. A toxoid is a bacterial toxin whose toxicity has been weakened or suppressed while other properties, typically immunogenicity, are maintained. As a class, bacterial toxins and derivatives thereof tend to be highly immunogenic. Polypeptide carriers derived from bacterial toxins have proven to be effective polypeptide carriers in vaccines. Generally, steps are taken (e.g., by chemical and/or genetic means) to render the toxins non-toxic and safe for administration to mammals. Examples of such bacterial toxin-derived polypeptide carriers which are currently commonly used in vaccine compositions, and may be used in conjugate antigens of vaccines useful in the provided methods, include the diphtheria and tetanus toxoids, and variants thereof (e.g., DT, DT $CRM_{197}$, TT), cholera toxoid, pertussis toxoid, inactivated or mutant pneumococcal pneumolysin, pneumococcal surface protein A or a derivative thereof, pneumococcal adhesion protein A or a derivative thereof, C5a peptidase group a or group b *streptococcus* or a derivative thereof, non-typable *H. influenzae* P4 protein or a derivative thereof, non-typable *H. influenzae* P6 protein or a derivative thereof, *M. catarrhalis* uspA or a derivative thereof, keyhole limpet haemocyanin (KLH), OMPC from *N. meningitidis*, the purified protein derivative of tuberculin (PPD), and protein D from *Haemophilus influenzae* (EP 594610-B), or fragments of any of the foregoing. Fragments suitable for use include fragments encompassing T-helper epitopes, which are readily known or identified by one skilled in the art.

$CRM_{197}$ (Wyeth, Sanford, N.C.) is a non-toxic variant (i.e., toxoid) of diphtheria toxin isolated from cultures of *Corynebacterium diphtheria* strain C7 (β197) grown in casamino acids and yeast extract-based medium. $CRM_{197}$ is purified through ultra-filtration, ammonium sulfate precipitation, and ion-exchange chromatography. Alternatively, $CRM_{197}$ is prepared recombinantly in accordance with U.S. Pat. No. 5,614,382, which is hereby incorporated by reference. Other diphtheria toxoids are also suitable for use as carrier proteins.

Conjugation Methods

A variety of strategies for coupling polysaccharide antigens to polypeptide carriers are known in the art. For example, each of the following references discusses relevant methods: Dick and Burret, *Contrib Microbiol Immunol.* 10:48-114 (Cruse J M, Lewis R E Jr, eds; Basel, Krager, 1989); U.S. Pat. No. 4,372,945; U.S. Pat. No. 4,474,757; U.S. Pat. No. 4,673,574; U.S. Pat. No. 4,695,624; U.S. Pat. No. 4,882,317; U.S. Pat. No. 5,360,897; U.S. Pat. No. 5,371,197; U.S. Pat. No. 5,623,057; European Patent Application EP 0 497 524; and International Patent Publication WO 94/04195.

In some embodiments polysaccharide antigens are coupled to polypeptide carriers using CDAP (see, for example, WO 95/08348).

Existing Conjugated Vaccines

Pneumococcal conjugate vaccine compositions useful in the practice of the present invention have been prepared in the art. To name just a few examples:

Two different heptavalent conjugate vaccines have been developed that contain capsular polysaccharides from pneumococcal serotypes 4, 6B, 9V, 14, 18C, 19F, and 23F. Such vaccines are known as "7vPnC" vaccines because they contain 7 valencies (7v) of the pneumococcal polysaccharide (Pn) as a conjugate (C). The first of these 7vPnC vaccines was PREVNAR® (pneumococcal 7-valent conjugate vaccine [diphtheria $CRM_{197}$ protein]), developed by Wyeth Pharmaceuticals, Inc. (Philadelphia, Pa.). In PREVNAR® (pneumococcal 7-valent conjugate vaccine [diphtheria $CRM_{197}$ protein]), the polysaccharides are each conjugated to the non-toxic $CRM_{197}$ variant of diphtheria toxin. PREVNAR® (pneumococcal 7-valent conjugate vaccine [diphtheria $CRM_{197}$ protein]) is the first pneumococcal conjugate vaccine approved for use in humans in the United States, and is currently licensed for pediatric use. Description of the heptavalent conjugate vaccine, and production of the conjugates is described in U.S. Pat. Nos. 4,673,574, 4,902,506, and 5,360,897.

The other 7vPnC vaccine was generated and reported by Merck & Co., West Point, Pa. In this vaccine, the 7 capsular polysaccharides are conjugated to the outer membrane protein complex (OMPC) of *Neisseria meningitidis* (Merck 7vPnC-OMPC).

Wyeth reported a nonavalent conjugated pneumococcal vaccine, containing capsular polysaccharides from pneumoccal serotypes 1, 4, 5, 6B, 9V, 14, 18C, 19F and 23F, each conjugated to the non-toxic $CRM_{197}$ variant of diphtheria toxin (Huebner, R., et al., *Ped. Inf. Dis. J.,* 21:1004-1007, 2002). (Wyeth, 9vPnC-MnCC).

Furthermore, a 13-valent pneumococcal vaccine has been generated by Wyeth, which comprises the capsular polysaccharides 4, 6B, 9V, 14, 18C, 19F, 23F, 1, 3, 5, 7F, 6A, and 19A conjugated to $CRM_{197}$ variant of diphtheria toxin (U.S. Ser. No. 11/395,593, filed Mar. 31, 2006).

Two tetravalent conjugated pneumococcal vaccines have also been generated and reported by Sanofi-Aventis, Swiftwater, Pa. The first contains capsular polysaccharides of serotypes 6B, 14, 19F, and 23F individually conjugated to diphtheria toxoid (Aventis 4vPnD); and the second is the same polysaccharides conjugated to tetanus toxoid (Aventis 4vPnT).

GlaxoSmithKline has reported an eleven-valent conjugated pneumococcal vaccine, containing capsular polysaccharides from a different set of serotypes, namely 6B, 14, 19F, 23F, 1, 3, 4, 5, 7F, 9V, and 18C. These polysaccharide antigens are individually conjugated to protein D of *H. influenzae* (GlaxoSmithKline, 11vPnC D).

GlaxoSmithKline has also reported a ten-valent conjugated pneumococcal vaccine, containing capsular polysaccharides from serotypes 1, 4, 5, 6B, 7F, 9V, 14, 18C, 19F, and 23F. These polysaccharide antigens are individually conjugated to protein D of *H. influenzae* (GlaxoSmithKline, 10vPnC D).

Sanofi-Aventis has reported generation of yet additional eleven-valent conjugated pneumococcal vaccines, containing polysaccharide antigens from the same serotype set found in the Merck & Co., product (Merck 11vPnC OMPC). A first has been conjugated to tetanus toxoid (Aventis 11vPnC T, and another contains polysaccharide conjugated to two different polypeptide carriers. Specifically, capsular polysaccharides from serotypes 3, 6B, 14, and 18C are conjugated to diphtheria toxoid, whereas capsular polysaccharides from serotypes 1, 4, 5, 7F, 9V, 19F, and 23F are conjugated to tetanus toxoid (Aventis 11vPnCTD).

Sanofi-Aventis also has also reported generation of two different versions of an eight-valent conjugate pneumococcal vaccine, containing capsular polysaccharides of serotypes 3, 6B, 14, 19F, 4, 23F, 9V, and 18C. In one, the polysaccharide antigens are conjugated to diphtheria toxoid; in the other they are conjugated to tetanus toxoid (Aventis 8vPnC D or 8vPnCT.).

Immunization Schedule

According to the present invention, vaccine administration may involve delivery of only a single dose, or alternatively may involve an initial dose followed by one or several additional immunization doses, adequately spaced. An immunization schedule is a program for the administration of one or more specified doses of one or more specified pneumococcal vaccines, by one or more specified routes of administration, at one or more specified ages of a subject.

The present invention provides immunization methods that involve administering at least one dose of a pneumococcal conjugate vaccine to an adult subject. In some embodiments, the adult subject is older than about 50 years of age. In some embodiments the adult subject is older than about 65 years of age. In some embodiments, the adult subject has previously received one or more doses of an unconjugated pneumococcal polysaccharide vaccine; in other embodiments, the adult subject is naïve to pneumococcal vaccines. In some embodiments, the adult subject has previously been infected with, or exposed to infection by *S. pneumoniae*. In some embodiments of the present invention, the subject will receive one or more additional doses of a pneumococcal vaccine, which may be a conjugate vaccine or an unconjugated vaccine; in other embodiments, the subject will not receive further pneumococcal vaccinations.

As illustrated in the Exemplification, the present invention demonstrates that pneumococcal conjugate vaccines can induce a superior increase in antibody generation, and a superior functional antibody response in older subjects when compared with an unconjugated polysaccharide vaccine. In particular, when the 7vPnC conjugate vaccine was administered to vaccine-naïve individuals over 70 years of age, both antibody titers (measured by ELISA) and functional antibody levels (measured by OPA) were higher for 6 of 7 common serotypes than were observed with the 23vPS unconjugated polysaccharide vaccine. Furthermore, studies presented in the Exemplification confirmed results seen in other studies where an initial administration of polysaccharide vaccine (e.g., 23vPS) appears to induce hyporesponsiveness to subsequent vaccine administration, as measured by decreased antibody level or functional antibody responses to subsequent polysaccharide (e.g., 23vPS) or conjugate vaccine (e.g., 7vPnC) administration. while this is not seen after PnC vaccine.

Immunization schedules of the present invention are provided to elicit or induce an immune response (e.g., an immuno-protective response) in an older subject sufficient to reduce at least one measure selected from the group consisting of incidence, prevalence, frequency and severity of at least one pneumococcal disease or disorder, and/or at least one surrogate marker of the disorder, in a population and/or subpopulation of the subject(s). A supplemental immunization schedule is one which has this effect relative to the standard schedule which it supplements. A supplemental schedule may call for additional administrations and/or supraimmunogenic doses of polysaccharide(s) and/or conjugate(s) found in the standard schedule, or for the administration of vaccines not part of the standard schedule. A full immunization schedule of the present invention may comprise both a standard schedule and a supplemental schedule. Exemplary sample vaccination schedules are provided for illustrative purposes. Detailed descriptions of methods to assess immunogenic response discussed herein allow one to develop alterations to the sample immunization schedules without undue experimentation.

In one embodiment of the present invention, a first administration of a pneumococcal vaccine usually occurs when a subject is more than about 50 years old, more than about 55 years old, more than about 60 years old, more than about 65 years old, or more than about 70 years old.

In some embodiments of the invention, a single administration of conjugate vaccine is employed. It is possible that the purposes of the present invention can be served with a single administration, especially when one or more utilized vaccine polysaccharide(s) and/or conjugate(s) or combinations thereof is/are strong, and in such a situation a single dose schedule is sufficient to induce a lasting immunoprotective response.

In certain embodiments, it is desirable to administer two or more doses of pneumococcal vaccine, which may include one dose of conjugate and at least one additional dose of conjugate and/or unconjugated polysaccharide vaccine for greater immunoprotective efficacy and coverage. Thus, in some embodiments, a number of doses is at least two, at least three or more doses. There is no set maximum number of doses, however it is good clinical practice not to immunize more often than necessary to achieve the desired effect.

Without being bound by theory, a first dose of pneumococcal conjugate vaccine administered according to the invention may be considered a "priming" dose. In certain embodiments, more than one dose is included in an immunization schedule. In such a scenario, a subsequent dose may be considered a "boosting" dose.

A priming dose may be administered to a naïve subject (a subject who has never previously received a pneumococcal polysaccharide vaccine, or a conjugate vaccine). In some embodiments, a priming dose may be administered to a subject who has previously received polysaccharide vaccine at least five or more years previous to administration of an initial conjugate vaccine according to the invention. In other embodiments, a priming dose may be administered to a subject who has previously received conjugate vaccine at least twenty or more years previous to administration of a priming conjugate vaccine according to the invention.

A boosting dose may be administered to an older subject who has previously received a conjugate vaccine. A boosting dose may comprise administration of a vaccine composition which is identical to the previously received priming dose. Alternatively and/or additionally, a boosting dose may comprise administration of a vaccine composition which is distinct from the previously received priming dose. In some embodiments, a boosting dose comprises at least one of the conjugate(s) of the previously received priming dose, and further comprises one or more additional conjugate(s) which were not contained in the priming dose. In other embodiments, a boosting dose comprises at least some of the conjugate(s) of the previously received priming dose, and further comprises one or more additional polysaccharide(s) which were not contained in the priming dose. In still other embodiments, a boosting dose comprises polysaccharide(s) which were not contained in the priming dose, and the boosting dose does not comprise conjugate(s) which were contained within the priming dose. Any number of boosting doses may be indicated to maintain an immunoprotective effect against *S. pneumoniae* infection.

When an immunization schedule calls for two or more separate doses, the interval between doses is considered. The interval between two successive doses may be the same throughout an immunization schedule, or it may change as the subject ages. In immunization schedules of the present invention, once a first vaccine dose has been administered, there is a first interval before administration of a subsequent dose. A first interval is generally at least about two weeks, one month, six weeks, two months, three months, six months, nine months, 12 months, or longer. Where more than one subsequent dose(s) are administered, second (or higher) intervals may be provided between such subsequent doses. In some embodiments, all intervals between subsequent doses are of the same length; in other embodiments, second intervals may vary in length. In some embodiments, the interval between subsequent doses may be at least about twelve months, at least about fifteen months, at least about eighteen months, at least about twenty-one months or at least about two years. In certain embodiments, the interval between doses may be up to three years, up to about four years, or up to about five years or ten years or more. In certain embodiments, intervals between subsequent doses may decrease as the subject ages.

The timing of the initial dose and the intervals between successive doses together determine how many doses occur within a particular period in a subject's life.

As noted above, exemplary sample schedules are provided herein. Sample Schedule 1 is an intensive immunization schedule where a recipient is immunized after about age 50 and receives subsequent pneumococcal immunizations every year. In addition to pneumococcal vaccination, an additional vaccine may be optionally included for administration (e.g., influenza vaccination). All vaccines are administered during each scheduled immunization. Vaccines may be continued for different durations of time.

Sample Schedule 2 is another possible immunization schedule. Immunization is initiated after about age 50. As in Schedule 1, vaccination may be optionally continued or omitted for different durations of time.

Sample Schedule 3 is a third possible immunization schedule. Vaccination is initiated in a subject after about age 50 and immunization continues every five years. After about age 60 subsequent immunization dosing may be administered at about every two years. After about age 65, subsequent immunization may be administered at about every year. Additional vaccines may be optionally included (e.g., influenza vaccine), and vaccines may be added or omitted or continued for different durations of time.

Sample Schedule 4 is yet another possible immunization schedule. Vaccination of a subject may have been previously initiated with polysaccharide (unconjugated) pneumococcal vaccine. In this schedule, vaccination is re-initiated with a conjugate vaccine after about age 60, or after about age 65. An initial dose of conjugate vaccine may be administered after about five years following an initial dose of pneumococcal polysaccharide vaccine. Optionally, subsequent vaccine doses may be included. Subsequent vaccine doses may be administered at about two years following the initial prime dose, or at about one year following the initial priming dose, depending on the subject. In some aspects, a subject may continue according to one of Schedules 1-3 described above after initial re-priming with conjugate vaccine.

It will be appreciated by those skilled in the art that a variety of possible combinations and subcombinations of the various conditions of timing of the first administration, shortest interval, largest interval and total number of administrations (in absolute terms, or within a stated period) exist, and all of these combinations and subcombinations should be considered to be within the inventor's contemplation though not explicitly enumerated here.

Assays for Determination of Immunogenic Response

It may often be desirable to assess the immunological response or responses achieved in subjects who receive one or more pneumococcal vaccine administrations according to the present invention. Any of a variety of methods may be used in such assessments.

Generally speaking, it may be desirable to assess humoral responses, cellular responses, and/or interactions between the two. Where humoral responses are being assessed, antibody titers and/or types (e.g., total IgG, IgG1, IgG2, IgM, IgA, etc.) to specific pneumococcal serotypes may be determined, for example before and/or after administration of an initial or a boosting dose of vaccine (and/or as compared with antibody levels in the absence of antigenic stimulation). Cellular responses may be assessed by monitoring reactions such as delayed type hypersensitivity responses, etc. to the carrier protein. Precursor and memory B cell populations may be assessed in ELISpot assays directed against specific pneumococcal capsular polysaccharides.

Any of a variety of assays may be employed to detect levels and/or activity of antibodies in subject sera. Suitable assays include, for example, ligand binding assays, such as radioimmunoassay (RIAs), enzyme-linked immunosorbent assays (ELISAs), and multiplex assays (Luminex, Bioplex); functional assays, such as opsonophagocytic assays (OPA); and in vivo protection assays (infant rat protection and adult mouse lung colonization and mortality models).

The RIA method detects type specific antibodies through incubation of sera with radio-labeled type-specific polysaccharides in suspension (see, e.g., Schiffman et al., J. Immunol. Meth. 33:133-144. 1980). The antigen-antibody complexes are then precipitated with ammonium sulfate and the radiolabeled pellets assayed for counts per minute (cpm).

In the ELISA detection method, serotype-specific antibodies from the sera of vaccinated subjects are quantitated by incubation with serotype-specific polysaccharides which have been adsorbed to a solid support (see, e.g., Koskela & Leinonen, J. Clin. Pathol. 34:93-98, 1981; Kojima et al., 1990, Tohoku J. Exp. Med. 161:209-215, 1990; Concepcion and Frasch, 2001. Clin Lab Diagn Immunol. 8: 266-272). The bound antibody is detected using enzyme-conjugated secondary detection antibodies. The ELISA also allows isotyping and subclassing of the immune response (i.e. IgM vs. IgG or IgG1 vs. IgG2) by using isotype- or subclass-specific secondary antibodies and can be adapted to evaluate the avidity of the serotype-specific antibodies (Anttila, et al, 1998. J. Infect Dis. 177:1614; Romero-Steiner, et al. 2005. Clin Lab Diagn Immunol 12: 1029-1035) Multiplex assays (e.g. Luminex, Bioplex) enable the simultaneous detection of antibodies to multiple serotypes. Serotype-specific capsular polysaccharides are conjugated to spectrally distinct microspheres, which are mixed together and incubated with diluted serum. Bound antibody is detected with a phycoerythrin-conjugated secondary antibody and is quantitated in a specialized flow cytometer that uses one laser to identify the bead type (serotype) and a second laser to quantitate the bound secondary antibody (Pickering, et al. 2002. Am. J, Clin. Pathol. 117:589-596; Lal, et al. 2005. J. Immunol Methods 296: 135-147).

An approach for assessing functional antibody in serum is the opsonophagocytic assay (OPA)) which quantitates only the antibodies that can opsonize the bacteria, leading to ingestion and killing of the bacteria. The standard assay utilizes a human phagocytic effector cell, a source of complement, encapsulated pneumococci, and diluted sera. The assay readout is the serum endpoint titer at which ≥50 of the input CFUs (i.e., bacteria) are killed in the assay (Romero-Steiner, et al, 1997. Clin. Diagn. Lab. Immunol. 4:415-422) This killing OPA can also be multiplexed by utilizing target strains of pneumococci that carry different antibiotic resistance markers (Kim, et al. 2003. Clin Lab Diagn Immunol. 10: 616-621). An endpoint titer of 1:8 or greater is considered a positive result in these killing type OPA. Another type of multiplex opsonic assay is a nonkilling assay in which the uptake by phagocytic effector cells of fluorescent stained encapsulated pneumococci or fluorescent microspheres conjugated with pneumococcal capsular polysaccharides in the presence of diluted sera plus a complement source is evaluated by flow cytometry (Martinez, et al. 1999. Clin Lab Diagn Immunol. 6: 581-586). Opsonic activity of serum antibody plus complement can also be evaluated by measuring the oxidative response of phagocytic human effector cells to ingested pneumococci (Munro, et al. 1985. Clin Exp Immunol 61: 183-188; Ojo-Amaize, et al. 1995. Clin Lab Diagn Immunol 2: 286-290).

Certain in vivo model systems can be used to evaluate the protection afforded by serum antibodies elicited by pneumococcal vaccines. In such passive protection systems, mice or infant rats are challenged with encapsulated pneumococci plus diluted human sera, and the endpoint titer of the sera which provides protection against bacteremia, lung colonization, or mortality is determined (Stack, et al. 1998. J Infect Dis. 177: 986-990; Saeland, et al. 2000. Microb Pathog 29: 81-91).

Vaccine Compositions and Administration

According to the present invention, pneumococcal vaccines are used to protect or treat a subject susceptible to or suffering from *S. pneumoniae* infection. In certain embodiments, the subject is an older subject. In some embodiments, the subject is an elderly subject. In some embodiments, the subject is naïve.

Any individual who suffers from a pneumococcal disease or who is at risk of developing a pneumococcal disease may be treated. It will be appreciated that an individual can be considered at risk for developing a disease without having been diagnosed with any symptoms of the disease. For example, if the individual is known to have been, or to be intended to be, in situations with relatively high risk of exposure to pneumococcal infection, that individual will be considered at risk for developing the disease (e.g., an elderly subject living in long term care facility). Similarly, if members of an individual's family or friends, or other close contacts have been diagnosed with pneumococcal infection, the individual may be considered to be at risk for developing the disease. Other exposures can include crowding, cigarette smoking, indoor smoke exposure ie wood burning stoves associated with certain groups, eg American Indians, etc).

Any effective route of administration may be utilized such as, for example, orally, nasally, enterally, parenterally, intramuscularly or intravenously, subcutaneously, intradermally, rectally, vaginally, topically, ocularly, pulmonarily, or by contact application. In some embodiments, vaccine compositions may be injected (e.g., via intramuscular, intraperitoneal, intradermal and/or subcutaneous routes); or delivered via the mucosa (e.g., to the oral/alimentary, respiratory, and/or genitourinary tracts). Intranasal administration of vaccines may be particularly useful in some contexts, for example for treatment of pneumonia or otitis media (as nasopharyngeal carriage of pneumococci can be more effectively prevented, thus attenuating infection at its earliest stage). In some embodiments of the invention, it may be desirable to administer different doses of a vaccine by different routes; in some embodiments, it may be desirable to administer different components of one dose via different routes.

In some embodiments of the present invention, vaccines are administered intradermally. Conventional technique of intradermal injection, the "mantoux procedure", comprises steps of cleaning the skin, and then stretching with one hand, and with the bevel of a narrow gauge needle (26-31 gauge) facing upwards the needle is inserted at an angle of between 10-15". Once the bevel of the needle is inserted, the barrel of the needle is lowered and further advanced while providing a slight pressure to elevate it under the skin. The liquid is then injected very slowly thereby forming a bleb or bump on the skin surface, followed by slow withdrawal of the needle.

Devices that are specifically designed to administer liquid agents into or across the skin have been described, for example the devices described in WO 99/34850 and EP 1092444, also the jet injection devices described for example in WO 01/13977; U.S. Pat. No. 5,480,381, U.S. Pat. No. 5,599,302, U.S. Pat. No. 5,334,144, U.S. Pat. No. 5,993,412, U.S. Pat. No. 5,649,912, U.S. Pat. No. 5,569,189, U.S. Pat. No. 5,704,911, U.S. Pat. No. 5,383,851, U.S. Pat. No. 5,893, 397, U.S. Pat. No. 5,466,220, U.S. Pat. No. 5,339,163, U.S. Pat. No. 5,312,335, U.S. Pat. No. 5,503,627, U.S. Pat. No. 5,064,413, U.S. Pat. No. 5,520,639, U.S. Pat. No. 4,596,556, U.S. Pat. No. 4,790,824, U.S. Pat. No. 4,941,880, U.S. Pat. No. 4,940,460, WO 97/37705 and WO 97/13537. Other methods of intradermal administration of the vaccine preparations may include conventional syringes and needles, or devices designed for ballistic delivery of solid vaccines (WO 99/27961), or transdermal patches (WO 97/48440; WO 98/28037); or applied to the surface of the skin (transdermal or transcutaneous delivery WO 98/20734; WO 98/28037).

As described above, vaccines may be administered as a single dose or as multiple doses. It will be appreciated that an administration is a single "dose" so long as all relevant components are administered to a subject within a window of time; it is not necessary that every component be present in a single composition. For example, administration of two different antigen (e.g., polysaccharide(s), or conjugate(s), or combination(s) thereof, or of two packets of the same antigen, within a period of less than 24 hours, is considered a single dose. To give but one example, polysaccharide antigens (or conjugates) from different pneumococcal serotypes may be administered in different compositions, but as part of a single dose. As noted above, such different compositions may be administered via different routes or via the same route. Alternatively or additionally, in embodiments wherein a vaccine comprises combination of polysaccharide antigen(s) (or conjugates) and additional types of active agents, polysaccharide (or conjugate) may be administered via one route, and a second active agent may be administered by a different route.

Vaccine compositions are administered in such amounts and for such time as is necessary to achieve a desired result. In certain embodiments of the present invention, a vaccine composition comprises an immunogenic amount of at least one pneumococcal polysaccharide or conjugate. As used herein, an "immunogenic" amount of the vaccine composition is an amount which is suitable to elicit an immune response. Thus, the amount effective to treat, attenuate, or prevent disease, as used herein, refers to a nontoxic but sufficient amount of the vaccine composition to treat, attenuate, or prevent disease in any subject. For example, the "therapeutically effective amount" can be an amount to treat, attenuate, or prevent infection (e.g., bacterial infection, pneumococcal infection), etc. The exact amount required to achieve a "immunogenic amount" may vary, depending on the particular component (e.g., polysaccharide, conjugate), and from subject to subject, depending on the species, age, and general condition of the subject, the stage of the disease, the particular pharmaceutical mixture, its mode of administration, and the like.

The amount of polysaccharide(s) antigen or conjugate(s) in each vaccine dose is selected to allow the vaccine, when administered as described herein, to induce an appropriate immunoprotective response without significant, adverse side effects A "immuno-protective" or "protective immune" response as used herein is an immune response sufficient to protect an immunized subject from productive infection by a particular pathogen or pathogens to which a vaccine is directed (e.g., *S. pneumoniae* infection). Such amounts may vary depending upon which specific polysaccharide(s) or conjugate(s), or combinations of polysaccharide(s) and/or conjugate(s) is employed and how it is presented. Generally, it is expected that each dose will comprise 0.1-100 μg of polysaccharide, about 0.1-50 μg, about 0.1-10 μg, or about 1 to 5 μg.

Optimal amounts of components for a particular vaccine can be ascertained by standard studies involving observation of appropriate immune responses in subjects. Following an initial vaccination, subjects can receive one or several booster immunizations adequately spaced in time.

Pneumococcal polysaccharide antigens (or conjugates thereof), and/or preparations thereof may be formulated in a unit dosage form for ease of administration and uniformity of dosage. The expression "unit dosage form," as used herein, refers to a physically discrete unit of vaccine composition appropriate for the patient to be treated. The specific therapeutically effective dose level for any particular patient or organism may depend upon a variety of factors including the severity or degree of risk of infection; the activity of the specific vaccine or vaccine composition employed; other characteristics of the specific vaccine or vaccine composition employed; the age, body weight, general health, sex of the subject, diet of the subject, pharmacokinetic condition of the subject, the time of administration (e.g., with regard to other activities of the subject such as eating, sleeping, receiving other medicines including other vaccine doses, etc.), route of administration, rate of excretion of the specific vaccine or vaccine composition employed; vaccines used in combination or coincidental with the vaccine composition employed; and like factors well known in the medical arts.

Pneumococcal vaccines for use in accordance with the present invention may be formulated according to known techniques. Vaccine preparation is generally described in Vaccine Design ("The subunit and adjuvant approach" (eds Powell M. F. & Newman M. J., Plenum Press New York, 1995). For example, an immunogenic amount of a vaccine product can be formulated together with one or more organic or inorganic, liquid or solid, pharmaceutically suitable carrier materials. Preparation of pneumococcal polysaccharide and conjugate vaccines is described, for example, in U.S. Ser. No. 11/395,593, filed Mar. 31, 2006, the contents of which are incorporated herein by reference.

In general, pharmaceutically acceptable carrier(s) include solvents, dispersion media, and the like, which are compatible with pharmaceutical administration. For example, materials that can serve as pharmaceutically acceptable carriers include, but are not limited to sugars such as lactose, glucose, dextrose, and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; polyols such as glycerol, propylene glycol, and liquid polyethylene glycol; esters such as ethyl oleate and ethyl laurate; agar; buffering agents such as magnesium hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as preservatives, and antioxidants can also be present in the composition, according to the judgment of the formulator (see also *Remington's Pharmaceutical Sciences*, Fifteenth Edition, E.W. martin (Mack Publishing Co., Easton Pa., 1975).

As is well known, vaccines may be formulated by combining polysaccharide antigens (and/or conjugates) with carriers and/or other optional components by any available means including, for example, conventional mixing, granulating, dissolving, lyophilizing, or similar processes.

Vaccine compositions useful in the provided methods may be lyophilized up until they are about to be used, at which point they are extemporaneously reconstituted with diluent. In some embodiments, vaccine components or compositions are lyophilized in the presence of one or more other components (e.g., adjuvants), and are extemporaneously reconstituted with saline solution. Alternatively, individual components, or sets of components may be separately lyophilized and/or stored (e.g., in a vaccination kit), the components being reconstituted and either mixed prior to use or administered separately to the subject.

Lyophilization can produce a more stable composition (for instance by preventing or reducing breakdown of polysaccharide antigens. Lyophilizing of vaccines or vaccine components is well known in the art. Typically, a liquid vaccine or vaccine component is freeze dried, often in the presence of an anti-caking agent (such as, for example, sugars such as sucrose or lactose). In some embodiments, the anti-caking agent is present, for example, at an initial concentration of 10-200 mg/mL. Lyophilization typically occurs over a series of steps, for instance a cycle starting at −69° C., gradually adjusting to −24° C. over 3 hours, then retaining this temperature for 18 hours, then gradually adjusting to −16° C. over 1 hour, then retaining this temperature for 6 hours, then gradually adjusting to +34° C. over 3 hours, and finally retaining this temperature over 9 hours.

Vaccines or vaccine components for use in accordance with the present invention may be incorporated into liposomes, cochleates, biodegradable polymers such as poly-lactide, poly-glycolide and poly-lactide-co-glycolides, or ISCOMS (immunostimulating complexes).

In certain situations, it may be desirable to prolong the effect of a vaccine or for use in accordance with the present invention, for example by slowing the absorption of one or more vaccine components. Such delay of absorption may be accomplished, for example, by the use of a liquid suspension of crystalline or amorphous material with poor water solubility. The rate of absorption of the product then depends upon its rate of dissolution, which in turn, may depend upon size and form. Alternatively or additionally, delayed absorption may be accomplished by dissolving or suspending one or more vaccine components in an oil vehicle. Injectable depot forms can also be employed to delay absorption. Such depot forms can be prepared by forming microcapsule matrices of one or more vaccine components a biodegradable polymers network. Depending upon the ratio of polymer to vaccine component, and the nature of the particular polymer(s) employed, the rate of release can be controlled.

Examples of biodegradable polymers that can be employed in accordance with the present invention include, for example, poly(orthoesters) and poly(anhydrides). One particular exemplary polymer is polylactide-polyglycolide.

Depot injectable formulations may also be prepared by entrapping the product in liposomes or microemulsions, which are compatible with body tissues.

Polymeric delivery systems can also be employed in non-depot formulations including, for example, oral formulations. For example, biodegradable, biocompatible polymers such as ethylene vinyl acetate, polyanhydrides, polyglycolic acid, collagen, polyorthoesters, and polylactic acid, etc., can be used in oral formulations. Polysaccharide antigens or conjugates may be formulated with such polymers, for example to prepare particles, microparticles, extrudates, solid dispersions, admixtures, or other combinations in order to facilitate preparation of useful formulations (e.g., oral).

Additional Vaccine Components and Combinations

Vaccines for use in accordance with the present invention include pneumococcal polysaccharides (and/or conjugates), and may additionally include one or more additional active agents (i.e., agents that exert a biological effect—not inert ingredients). It will be appreciated that such additional agents may be formulated together with one or more other vaccine components, or may be maintained separately and combined at or near the time of administration. In some embodiments, such additional components may be administered separately from some or all of the other vaccine components, within an appropriate time window for the relevant effect to be achieved.

For example, it is common in vaccine preparation to include one or more adjuvants. Adjuvants, generally, are agents that enhance the immune response to an antigen. In some embodiments, adjuvants that enhance a Th1-type immune response are utilized.

To give but a few examples, adjuvants that are suitable for use in accordance with the present invention include, but are not limited to:

(1) aluminum salts (alum), such as aluminum hydroxide, aluminum phosphate, aluminum sulfate, etc.;

(2) oil-in-water emulsion formulations (with or without other specific immunostimulating agents such as muramyl peptides (defined below) or bacterial cell wall components), such as, for example, (a) MF59 (PCT Publ. No. WO 90/14837), containing 5% Squalene, 0.5% TWEEN 80 (polysorbate 80), and 0.5% Span 85 (optionally containing various amounts of MTP-PE (see below, although not required)) formulated into submicron particles using a microfluidizer such as Model 110Y microfluidizer (Microfluidics, Newton, Mass.), (b) SAF, containing 10% Squalene, 0.4% TWEEN 80 (polysorbate 80), 5% pluronic-blocked polymer L121, and thr-MDP (see below) either microfluidized into a submicron emulsion or vortexed to generate a larger particle size emulsion, and (c) Ribi™ adjuvant system (RAS), (Corixa, Hamilton, Mont.) containing 2% Squalene, 0.2% TWEEN 80 (polysorbate 80), and one or more bacterial cell wall components from the group consisting of 3-O-deaylated monophosphorylipid A (MPL™) described in U.S. Pat. No. 4,912,094 (Corixa), trehalose dimycolate (TDM), and cell wall skeleton (CWS), preferably MPL+CWS (Detox™);

(3) saponin adjuvants, such as Quil A or STIMULON™ QS-21 (Antigenics, Framingham, Mass.) (U.S. Pat. No. 5,057,540) may be used or particles generated therefrom such as ISCOMs (immunostimulating complexes);

(4) bacterial lipopolysaccharides, synthetic lipid A analogs such as aminoalkyl glucosamine phosphate compounds (AGP), or derivatives or analogs thereof, which are available from Corixa, and which are described in U.S. Pat. No. 6,113,918; one such AGP is 2-[(R)-3-Tetradecanoyloxytetradecanoylamino]ethyl 2-Deoxy-4-O-phosphono-3-O—[(R)-3-tetradecanoyloxytetradecanoyl]-2-[(R)-3-tetradecanoyloxytetradecanoylamino]-b-D-glucopyranoside, which is also know as 529 (formerly known as RC529), which is formulated as an aqueous form or as a stable emulsion, synthetic polynucleotides such as oligonucleotides containing CpG motif(s) (U.S. Pat. No. 6,207,646);

(5) cytokines, such as interleukins (e.g., IL-1, IL-2, IL-4, IL-5, IL-6, IL-7, IL-12, IL-15, IL-18, etc.), interferons (e.g., gamma interferon), granulocyte macrophage colony stimulating factor (GM-CSF), macrophage colony stimulating factor (M-CSF), tumor necrosis factor (TNF), costimulatory molecules B7-1 and B7-2, etc.;

(6) detoxified mutants of a bacterial ADP-ribosylating toxin such as a cholera toxin (CT) either in a wild-type or mutant form, for example, where the glutamic acid at amino acid position 29 is replaced by another amino acid, preferably a histidine, in accordance with published international patent application number WO 00/18434 (see also WO 02/098368 and WO 02/098369), a pertussis toxin (PT), or an *E. coli* heat-labile toxin (LT), particularly LT-K63, LT-R72, CT-S109, PT-K9/G129 (see, e.g., WO 93/13302 and WO 92/19265); and (7) other substances that act as immunostimulating agents to enhance the effectiveness of the composition.

Muramyl peptides include, but are not limited to, N-acetyl-muramyl-L-threonyl-D-isoglutamine (thr-MDP), N-acetyl-normuramyl-L-alanine-2-(1'-2' dipalmitoyl-sn-glycero-3-hydroxyphosphoryloxy)-ethylamine (MTP-PE), etc.

Vaccines for use in accordance with the present invention may include one or more bacterial toxins and/or their attenuated derivatives (i.e., not in the form of a polysaccharide conjugate). The compositions of this invention may also include one or more proteins from *Streptococcus pneumoniae*. Examples of *Streptococcus pneumoniae* proteins suitable for inclusion include those identified in International Patent Application WO02/083855, as well as that described in International Patent Application WO02/053761. Alternatively or additionally, such vaccines may include one or more other bacterial antigens such as, for example, PhtA, PhtD, PhtB, PhtE, SpsA, LytB, LytC, LytA, Sp125, Sp101, Sp128, Sp130 and Sp133, and combinations thereof.

Vaccines for use in accordance with the present invention may include, or be administered concurrently with, other antimicrobial therapy. For example, such vaccines may include or be administered with one or more agents that kills or retards growth of *S. pneumoniae*. Such agents include, for example, penicillin, vancomycin, erythromycin, azithromycin, and clarithromycin, cefotaxime, ceftriaxone, levoflaxin, gatifloxacin.

Alternatively or additionally, vaccines for use in accordance with the present invention may include, or be administered with, one or more other vaccines or therapies. For example, one or more non-pneumococcal antigens may be included in or administered with the vaccines.

The compositions of this invention may further include one or more additional antigens for use against otitis media caused by infection with other bacteria. Such bacteria include nontypable *Haemophilus influenza, Moraxella catarrhalis* (formerly known as *Branhamella catarrhalis*) and *Alloiococcus otitidis*.

Examples of nontypable *Haemophilus influenzae* antigens suitable for inclusion include the P4 protein, also known as protein "e" (U.S. Pat. No. 5,601,831; International Patent Application WO03/078453), the P6 protein, also known as the PAL or the PBOMP-1 protein (U.S. Pat. No. 5,110,908; International Patent Application WO0100790), the P5 protein (U.S. Reissue Pat. No. 37,741), the *Haemophilus* adhesion and penetration protein (U.S. Pat. Nos. 6,245,337 and 6,676,948), the LKP tip adhesin protein (U.S. Pat. No. 5,643,725) and the NucA protein (U.S. Pat. No. 6,221,365).

Examples of *Moraxella catarrhalis* antigens suitable for inclusion include the UspA2 protein (U.S. Pat. Nos. 5,552,146, 6,310,190), the CD protein (U.S. Pat. No. 5,725,862), the E protein (U.S. Pat. No. 5,948,412) and the 74 kilodalton outer membrane protein (U.S. Pat. No. 6,899,885).

Examples of *Alloiococcus otitidis* antigens suitable for inclusion include those identified in International Patent Application WO03/048304.

The compositions of this invention may further include one or more proteins from *Neisseria meningitidis* type B. Examples of *Neisseria meningitidis* type B proteins suitable for inclusion include those identified in International Patent Applications WO03/063766, WO2004/094596, WO01/85772, WO02/16612 and WO01/87939.

Further additional antigens may comprise antigens of other infectious diseases such as, but not limited to, hepatitis A, hepatitis B, influenza, meningitis, polio virus, tetanus, varicella, diphtheria, measles, mumps, and rubella. Certain exemplary antigens include, but are not limited to Hepatitis B surface antigen (HBsAg), *Moraxella catarrhalis* outer membrane proteins, non-typable *Haemophilus influenzae* proteins, *N. meningitidis* B outer membrane proteins. Other combinations contemplated are the pneumococcal PS & protein of the invention in combination with viral antigens, for example, from influenza (attenuated, split, or subunit [e.g., surface glycoproteins neuraminidase (NA) and haemagglutinin (HA). See, e.g., Chaloupka I. et al, Eur. Journal Clin. Microbiol. Infect. Dis. 15:121-127, 1996], RSV (e.g., F and G antigens or F/G fusions, see, eg, Schmidt A. C. et al, J Virol, p 4594-4603, 2001), and PIV3 (e.g., HN and F proteins, see Schmidt et al. supra).

In order that the invention described herein may be more fully understood, the following examples are set forth. The representative examples contain information, exemplification and guidance, which can be adapted to the practice of this invention in its various embodiments and the equivalents thereof. It should be understood that these examples are for illustrative purposes only and are not to be construed as limiting this invention in any manner.

EXEMPLIFICATION

Example 1

Dose Ranging Study in Naïve Adults ≥70 Years

A dose-ranging study was carried out which compared the safety, tolerability and immunogenicity of pneumococcal conjugate vaccine at three dosage levels with pneumococcal polysaccharide unconjugated vaccine in ambulatory elderly adults aged 70 years and older. Immune response to a single injection was measured for each of three dose levels of 7vPnC vaccine (PREVNAR®, pneumococcal 7-valent conjugate vaccine (Diphtheria $CRM_{197}$ protein), Wyeth Pharmaceuticals, Inc., Philadelphia, Pa.), relative to the response to 23vPS vaccine (PNEUMOVAX® 23 (pneumococcal vaccine polyvalent), pneumococcal polysaccharide vaccine, Aventis Pasteur MSD, Ltd., Berkshire, UK). Safety and tolerability of a single injection of one of three dose levels of 7vPnC vaccine relative to that of 23vPS vaccine were also assessed.

Study Design

A total of 443 individuals, 70 years and older without prior 23vPS vaccination were enrolled in a randomized, open-label, and controlled, study. Three different dosage levels of pneumococcal conjugate vaccine representing 1×, 2×, and 4× the 7vPnC dosage were evaluated. Because no higher dosage for PREVNAR® (pneumococcal 7-valent conjugate vaccine [diphtheria $CRM_{197}$ protein]) 7vPnC formulations were available, the 2× dosage was approximated by mixing one vial of PREVNAR® (pneumococcal 7-valent conjugate vaccine [diphtheria $CRM_{197}$ protein]) 7vPnC at 2 µg/serotype (4 µg for serotype 6B) with one vial of lyophilized 9valent PnC vaccine (9vPnC) at 2 µg/serotype (containing additional serotypes 1 and 5). The 4× dosage was obtained by mixing two vials of PREVNAR® (pneumococcal 7-valent conjugate vaccine [diphtheria $CRM_{197}$ protein]) 7vPnC with 2 vials of 9-valent vaccine. Individuals were randomized in a 1:1:1:1 ratio to receive a single injection of one of the three conjugate formulations or a single injection of 23vPS.

TABLE 1

Dosing Plan for Adult Pneumococcal Dose Ranging Study

| Year 1 -- Dose 1 | | | Year 2 Dose 2 (12 months after Dose 1) | | |
|---|---|---|---|---|---|
| Group | N | Vaccine | Group | N | Vaccine |
| 1 | 100 | 1 × PREVNAR ® | 1a | 50 | 23vPS |
| | | | 1b | 50 | 1 × PREVNAR ® |
| 2 | 100 | 1 × PREVNAR ® + 1 × 9vPnC | 2a | 50 | 23vPS |
| | | | 2b | 50 | 1 × PREVNAR ® + 1 × 9vPnC |
| 3 | 100 | 2 × PREVNAR ® + 2 × 9vPnC | 3a | 50 | 23vPS |
| | | | 3b | 50 | 2 × PREVNAR ® + 2 × 9vPnC |
| 4 | 100 | 23vPS | 4 | 100 | PREVNAR ® |

PREVNAR ® refers to pneumococcal 7-valent conjugate vaccine [diphtheria $CRM_{197}$ protein].

Table 2 outlines the vaccines administered for the studies in this Example, as well as the second year Dose 2 studies described in Example 2.

TABLE 2

Vaccines administered in the Dose-ranging study

| Vaccines | Dose/ serotype (µg) | Total Polysaccharide Dose (µg) | CRM197 dose (µg) | Alum (mg) | Volume (ml) |
|---|---|---|---|---|---|
| PREVNAR ® | 2 (6B = 4 µg) | 16 | 18 | 0.125 | 0.5 |
| 1 × PREVNAR ® + 1 × 9vPnC | 4 (6B = 8 µg) | 40 | 37 | 0.125 | 0.5 |
| 2 × PREVNAR ® + 2 × 9vPnC | 8 (6B = 16 µg) | 80 | 74 | 0.250 | 1.0 |
| 23vPS | 25 | 575 | — | — | 0.5 |

PREVNAR ® refers to pneumococcal 7-valent conjugate vaccine [diphtheria $CRM_{197}$ protein].

Results from Single Dose of Vaccine.

A total of 443 subjects, with approximately 110 subjects per treatment group were vaccinated with PnC 2 µg/serotype (PREVNAR® (pneumococcal 7-valent conjugate vaccine [diphtheria $CRM_{197}$ protein]), 7vPnC), 4 µg PnC, 8 µg PnC, or 23vPS (PNEUMOVAX® 23 (pneumococcal vaccine polyvalent)). The groups were well balanced for demographics and pre-immunization antibody levels. Immune responses to vaccine were assessed by ELISA analyses to measure serotype specific antibody levels; and opsonophagocytosis (OPA) analyses to determine opsonic titer activity levels. Local and systemic reactions were assessed and recorded up to two weeks post vaccination dosing.

ELISA results for 7 serotypes following a single vaccine dose are shown in Table 3. The ELISA geometric mean antibody concentration (GMCs) for 7vPnC were superior to 23vPS for all but one (serotype 19F) of the serotypes assessed, demonstrating increased levels of mean antibody concentration for the conjugate vaccine treatment group as compared to the unconjugated polysaccharide vaccine treatment group, for six of the seven serotypes assessed.

Initial OPA results for serotypes 6B, 9V, 18C, 19F and 23F, following a single dose of vaccine are shown in Table 4. The OPA geometric mean titers (GMTs) for 7vPnC were superior to 23vPS for serotypes 9V, 18C, 23F, demonstrating increased activity against three of five serotypes assessed.

For all responses and reactions recorded, pain at the injection site and redness were the most frequently observed local reactions after dose 1. Pain at the injection site and redness were comparable between the 7vPnC and 23vPS groups with a trend toward higher responses in the 7vPnC group. See Table 5 and Table 6 for a summary of the safety and tolerability assessment results following a single dose of vaccine. Safety and tolerability between 7vPnC and 23vPS were comparable with a trend toward higher responses in the 7vPnC group, as the 4 μg dose was also comparable to the 23vPS, while the 8 μg dose produced higher local reactogenicity. The incidence of injection site events and systemic reactions were acceptable for all groups tested.

TABLE 3

Post Dose 1 Pneumococcal ELISA Geometric Mean Antibody Concentrations (μg/mL) (Dose 1 All-Available Immunogenicity Population)

| Serotype | Randomized Treatment Group | N[b] | Sampling Time[a] 1 Month Post Dose 1 GMC[c] | 95% CI[d] |
|---|---|---|---|---|
| 4 | 7vPnC | 110 | 3.1 | (2.2, 4.3) |
|   | 23vPS | 107 | 1.4 | (1.1, 2.0) |
| 6B | 7vPnC | 110 | 8.0 | (6.0, 10.8) |
|   | 23vPS | 107 | 4.4 | (3.4, 5.8) |
| 9V | 7vPnC | 110 | 9.8 | (7.5, 12.8) |
|   | 23vPS | 107 | 3.6 | (2.8, 4.6) |
| 14 | 7vPnC | 110 | 17.1 | (12.3, 24.0) |
|   | 23vPS | 107 | 8.5 | (6.0, 12.1) |
| 18C | 7vPnC | 110 | 13.0 | (10.1, 16.7) |
|   | 23vPS | 107 | 6.8 | (5.2, 8.9) |
| 19F | 7vPnC | 110 | 5.5 | (4.1, 7.4) |
|   | 23vPS | 107 | 4.4 | (3.4, 5.8) |
| 23F | 7vPnC | 110 | 12.4 | (9.0, 17.0) |
|   | 23vPS | 107 | 3.8 | (2.9, 5.0) |

[a]Protocol specified timing for blood sample.
[b]N = the number of subjects with assay results for the specified serotype and the given visit.
[c]Geometric Mean Concentrations (GMCs) were calculated using all subjects with available data for the specified blood draw.
[d]Confidence limits (CI) are back transforms of a confidence interval based on Student's t-distribution for the mean logarithm of the concentrations.

TABLE 4

Pneumococcal OPA Geometric Mean Antibody Titers for Dose 1 (Dose 1 Evaluable Immunogenicity Population)

| Serotype | Randomized Treatment Group | Pre-Dose 1 | | | 1 Month Post-Dose 1 | | | Fold Rise (Post/Pre) | | |
|---|---|---|---|---|---|---|---|---|---|---|
| | | N[b] | GMT[c] | 95% CI[d] | N[b] | GMT[c] | 95% CI[d] | N[b] | GMFR[e] | 95% CI[d] |
| 1 | 7vPnC | 99 | 22.7 | (16.9, 30.6) | 99 | 23.4 | (17.2, 31.8) | 99 | 1.0 | (0.8, 1.4) |
|   | 2x | 107 | 24.9 | (18.0, 34.4) | 108 | 306.4 | (214.9, 436.9) | 107 | 12.6 | (8.5, 18.6) |
|   | 4x | 107 | 23.1 | (17.2, 31.2) | 107 | 438.3 | (318.3, 603.5) | 107 | 18.9 | (13.2, 27.1) |
|   | 23vPS | 100 | 28.1 | (20.4, 38.6) | 100 | 147.0 | (103.8, 208.4) | 100 | 5.2 | (3.5, 7.8) |
| 4 | 7vPnC | 99 | 12.9 | (9.0, 18.4) | 99 | 1504.9 | (1025.0, 2209.6) | 99 | 116.9 | (71.5, 190.9) |
|   | 2x | 107 | 15.2 | (10.7, 21.6) | 108 | 1505.0 | (1015.2, 2231.1) | 107 | 98.1 | (57.5, 167.4) |
|   | 4x | 107 | 15.4 | (10.7, 22.1) | 107 | 2021.6 | (1490.5, 2742.1) | 107 | 131.4 | (82.9, 208.2) |
|   | 23vPS | 100 | 14.1 | (9.8, 20.3) | 100 | 661.7 | (447.9, 977.6) | 100 | 46.9 | (29.2, 75.3) |
| 5 | 7vPnC | 99 | 20.2 | (14.3, 28.5) | 99 | 17.9 | (13.3, 24.0) | 99 | 0.9 | (0.7, 1.2) |
|   | 2x | 107 | 21.0 | (15.0, 29.5) | 108 | 278.3 | (182.1, 425.2) | 107 | 13.2 | (8.5, 20.3) |
|   | 4x | 107 | 19.2 | (14.0, 26.4) | 107 | 444.0 | (286.3, 688.4) | 107 | 23.1 | (15.4, 34.7) |
|   | 23vPS | 100 | 21.7 | (16.0, 29.4) | 100 | 250.7 | (171.0, 367.7) | 100 | 11.6 | (7.5, 17.8) |
| 6B | 7vPnC | 96 | 64.0 | (39.0, 105.0) | 99 | 1526.2 | (1043.8, 2231.6) | 96 | 22.6 | (13.8, 37.0) |
|   | 2x | 100 | 74.0 | (45.1, 121.5) | 107 | 2536.1 | (1760.3, 3653.9) | 99 | 34.1 | (20.1, 57.9) |
|   | 4x | 98 | 52.9 | (32.9, 84.9) | 107 | 3914.4 | (2929.5, 5230.5) | 98 | 76.9 | (47.4, 124.8) |
|   | 23vPS | 93 | 57.7 | (34.2, 97.3) | 99 | 830.0 | (553.3, 1245.0) | 92 | 13.7 | (8.0, 23.2) |
| 9V | 7vPnC | 99 | 116.9 | (76.1, 179.5) | 99 | 3052.5 | (2193.3, 4248.1) | 99 | 26.1 | (15.3, 44.7) |
|   | 2x | 105 | 172.3 | (109.1, 272.1) | 108 | 3511.3 | (2547.1, 4840.3) | 105 | 21.1 | (13.3, 33.6) |
|   | 4x | 107 | 147.6 | (97.1, 224.4) | 107 | 5239.2 | (3976.8, 6902.4) | 107 | 35.5 | (21.9, 57.6) |
|   | 23vPS | 99 | 139.2 | (88.3, 219.4) | 99 | 981.9 | (697.5, 1382.2) | 98 | 6.9 | (4.4, 10.9) |
| 14 | 7vPnC | 99 | 110.5 | (63.0, 193.7) | 99 | 2526.7 | (1640.4, 3891.9) | 99 | 22.9 | (12.7, 41.3) |
|   | 2x | 107 | 112.4 | (67.6, 187.0) | 108 | 2547.4 | (1699.3, 3818.9) | 107 | 22.3 | (12.9, 38.6) |
|   | 4x | 107 | 68.3 | (41.0, 113.8) | 106 | 3433.1 | (2569.9, 4586.1) | 106 | 51.6 | (28.6, 93.0) |
|   | 23vPS | 100 | 93.7 | (55.6, 158.0) | 99 | 1024.0 | (628.7, 1667.8) | 99 | 11.1 | (6.4, 19.2) |
| 18C | 7vPnC | 99 | 47.4 | (32.3, 69.4) | 99 | 1364.5 | (937.6, 1985.8) | 99 | 28.8 | (18.4, 45.0) |
|   | 2x | 107 | 50.7 | (35.3, 72.9) | 108 | 1711.1 | (1159.6, 2525.1) | 107 | 33.9 | (21.3, 54.1) |
|   | 4x | 107 | 35.3 | (25.5, 48.8) | 106 | 2172.1 | (1497.1, 3151.6) | 106 | 61.9 | (41.6, 92.1) |
|   | 23vPS | 100 | 42.8 | (29.5, 62.1) | 100 | 458.3 | (302.7, 693.7) | 100 | 10.7 | (7.3, 15.6) |
| 19F | 7vPnC | 98 | 15.1 | (10.8, 21.1) | 99 | 200.4 | (130.3, 308.2) | 98 | 13.4 | (8.4, 21.4) |
|   | 2x | 106 | 14.5 | (10.4, 20.2) | 108 | 148.4 | (96.9, 227.1) | 106 | 10.5 | (6.9, 16.2) |
|   | 4x | 107 | 17.4 | (12.6, 24.1) | 106 | 359.7 | (246.9, 524.0) | 106 | 20.4 | (14.3, 29.1) |
|   | 23vPS | 100 | 12.2 | (8.9, 16.8) | 100 | 203.7 | (134.1, 309.3) | 100 | 16.7 | (10.8, 25.7) |

TABLE 4-continued

Pneumococcal OPA Geometric Mean Antibody Titers for Dose 1 (Dose 1 Evaluable Immunogenicity Population)

| Serotype | Randomized Treatment Group | Sampling Time[a] | | | | | | | | |
|---|---|---|---|---|---|---|---|---|---|---|
| | | Pre-Dose 1 | | | 1 Month Post-Dose 1 | | | Fold Rise (Post/Pre) | | |
| | | N[b] | GMT[c] | 95% CI[d] | N[b] | GMT[c] | 95% CI[d] | N[b] | GMFR[e] | 95% CI[d] |
| 23F | 7vPnC | 96 | 40.9 | (26.1, 64.0) | 99 | 1403.2 | (898.6, 2191.2) | 96 | 35.7 | (20.6, 61.8) |
| | 2x | 105 | 55.7 | (35.4, 87.7) | 106 | 1205.9 | (822.8, 1767.3) | 103 | 20.8 | (12.9, 33.6) |
| | 4x | 104 | 46.2 | (30.3, 70.3) | 105 | 1929.9 | (1370.1, 2718.3) | 102 | 39.2 | (24.9, 61.9) |
| | 23vPS | 99 | 44.8 | (28.7, 69.9) | 97 | 291.1 | (193.9, 437.1) | 96 | 6.1 | (4.2, 8.8) |

[a]Protocol specified timing for blood sample.
[b]N = Number of subjects with assay results for the specified serotype and the given visit.
[c]Geometric Mean Titers (GMTs) were calculated using all subjects with available data for the specified blood draw.
[d]Confidence limits (CI) are back transforms of a confidence interval based on Student's t-distribution for the mean logarithm of the concentrations or fold-rises.
[e]Geometric Mean Fold Rises (GMFRs) were calculated using all subjects with available data from both the pre-dose and post-dose blood draws.
2x = 9vPnC reconstituted with 7vPnC.
4x = 2 doses 9vPnC reconstituted with 2 doses 7vPnC.

TABLE 5

Number (%) of Subjects Reporting Injection Site Events Within 7 Days Following Dose 1

| | Actual Treatment Group | | | | | | | | | | | | |
|---|---|---|---|---|---|---|---|---|---|---|---|---|---|
| | 7vPnC | | | 2x | | | 4x | | | 23vPS | | | |
| Local Reaction | N[a] | n[b] | % | N[a] | n[b] | % | N[a] | n[b] | % | N[a] | n[b] | % | p-value[c] |
| Redness | | | | | | | | | | | | | |
| Any | 103 | 35 | 34.0 | 102 | 25 | 24.5 | 105 | 51 | 48.6 | 100 | 23 | 23.0 | 0.090 |
| Significant[d] | 99 | 12 | 12.1 | 102 | 12 | 11.8 | 101 | 34 | 33.7 | 99 | 9 | 9.1 | 0.645 |
| >7 cm[e] | 99 | 2 | 2.0 | 100 | 0 | 0.0 | 100 | 7 | 7.0 | 99 | 2 | 2.0 | >0.999 |
| Swelling | | | | | | | | | | | | | |
| Any | 102 | 20 | 19.6 | 100 | 16 | 16.0 | 106 | 44 | 41.5 | 99 | 17 | 17.2 | 0.718 |
| Significant[d] | 99 | 5 | 5.1 | 100 | 6 | 6.0 | 98 | 20 | 20.4 | 97 | 5 | 5.2 | >0.999 |
| >7 cm[e] | 99 | 0 | 0.0 | 98 | 0 | 0.0 | 97 | 3 | 3.1 | 97 | 1 | 1.0 | 0.495 |
| Pain at injection site | | | | | | | | | | | | | |
| Any | 104 | 40 | 38.5 | 106 | 34 | 32.1 | 109 | 58 | 53.2 | 104 | 26 | 25.0 | 0.052 |
| Significant[f] | 99 | 4 | 4.0 | 102 | 2 | 2.0 | 108 | 14 | 13.0 | 103 | 4 | 3.9 | >0.999 |
| Any Injection Site Reaction[g] | 106 | 57 | 53.8 | 105 | 46 | 43.8 | 108 | 82 | 75.9 | 100 | 43 | 43.0 | 0.128 |

[a]N represents the number of subjects with known values.
[b]n represents the number of subjects with the specified event.
[c]Fisher Exact test, two-sided, for percent of subjects between the 7vPnC and 23vPS groups.
[d]Significant is defined as having a diameter for the involved area >8 caliper units or 4.0 cm, including subjects with local reactions >7.0 cm.
[e]Subjects with local reactions >7.0 cm were encouraged not to return.
[f]Significant is defined as interfering with limb movement.
[g]Any injection site event includes any pain, any swelling, and any redness. Subjects were included in this category if they experienced an event or had 'no' for all days for all events (i.e., any missing value excludes the subject unless they experienced an event).
2x = 9vPnC reconstituted with 7vPnC.
4x = 2 doses 9vPnC reconstituted with 2 doses 7vPnC.

TABLE 6

Number (%) of Subjects Reporting Systemic Reactions Within 7 Days Following Dose 1

| | Actual Treatment Group | | | | | | | | | | | | |
|---|---|---|---|---|---|---|---|---|---|---|---|---|---|
| | 7vPnC | | | 2x | | | 4x | | | 23vPS | | | |
| Systemic Reaction | N[a] | n[b] | % | N[a] | n[b] | % | N[a] | n[b] | % | N[a] | n[b] | % | p-value[c] |
| Fever ≥38° C. | 101 | 1 | 1.0 | 106 | 2 | 1.9 | 110 | 3 | 2.7 | 104 | 3 | 2.9 | 0.621 |
| Fever >39° C. | 101 | 0 | 0.0 | 106 | 0 | 0.0 | 110 | 0 | 0.0 | 104 | 0 | 0.0 | >0.999 |
| Fever >40° C. | 101 | 0 | 0.0 | 106 | 0 | 0.0 | 110 | 0 | 0.0 | 104 | 0 | 0.0 | >0.999 |
| Fatigue | 106 | 24 | 22.6 | 108 | 23 | 21.3 | 112 | 23 | 20.5 | 105 | 22 | 21.0 | 0.868 |
| Headache | 104 | 11 | 10.6 | 108 | 15 | 13.9 | 112 | 17 | 15.2 | 106 | 14 | 13.2 | 0.671 |

TABLE 6-continued

Number (%) of Subjects Reporting Systemic Reactions Within 7 Days Following Dose 1

| | Actual Treatment Group | | | | | | | | | | | | |
|---|---|---|---|---|---|---|---|---|---|---|---|---|---|
| | 7vPnC | | | 2x | | | 4x | | | 23vPS | | | |
| Systemic Reaction | $N^a$ | $n^b$ | % | $N^a$ | $n^b$ | % | $N^a$ | $n^b$ | % | $N^a$ | $n^b$ | % | p-value$^c$ |
| Chills | 105 | 3 | 2.9 | 107 | 4 | 3.7 | 112 | 9 | 8.0 | 105 | 9 | 8.6 | 0.134 |
| Rash | 105 | 2 | 1.9 | 107 | 3 | 2.8 | 109 | 7 | 6.4 | 105 | 2 | 1.9 | >0.999 |
| Vomiting | 104 | 0 | 0.0 | 107 | 2 | 1.9 | 111 | 1 | 0.9 | 104 | 2 | 1.9 | 0.498 |
| Decreased appetite | 106 | 5 | 4.7 | 107 | 9 | 8.4 | 112 | 7 | 6.3 | 105 | 9 | 8.6 | 0.284 |
| Muscle pain | 105 | 20 | 19.0 | 103 | 13 | 12.6 | 111 | 26 | 23.4 | 106 | 14 | 13.2 | 0.267 |
| Joint pain | 103 | 8 | 7.8 | 106 | 12 | 11.3 | 108 | 12 | 11.1 | 101 | 6 | 5.9 | 0.783 |
| Medication to treat fever | 95 | 1 | 1.1 | 100 | 1 | 1.0 | 101 | 2 | 2.0 | 91 | 1 | 1.1 | >0.999 |
| Any new medications | 93 | 3 | 3.2 | 98 | 4 | 4.1 | 101 | 2 | 2.0 | 93 | 4 | 4.3 | >0.999 |
| Any Systemic Reaction$^d$ | 101 | 40 | 39.6 | 105 | 40 | 38.1 | 106 | 46 | 43.4 | 102 | 39 | 38.2 | 0.886 |

$^a$N represents the number of subjects with known values.
$^b$n represents the number of subjects with the specified event.
$^c$Fisher Exact test, two-sided, for percent of subjects between the 7vPnC and 23cPS groups.
$^d$Any systemic reaction excludes any new medications and any medications to treat a fever. Subjects were included in this category if they experienced an event or had 'no' for all days for all events (i.e., any missing value excludes the subject unless they experienced an event).
2x = 9vPnC reconstituted with 7vPnC;
4x = 2 doses 9vPnC reconstituted with 2 doses 7vPnC.

Summary of First Dose Study Results

As discussed above, the benefits of a conjugate vaccine in naïve adults compared to unconjugated polysaccharide vaccine include demonstrated higher antibody levels (ELISA) and better functional antibody activity (OPA) responses. Both could be demonstrated after a single dose, with an acceptable safety profile.

Example 2

Dose Ranging Study—Second Dosing

Study Design

See Study Design description in Example 1 above, and Table 1 and Table 2 for description of study, dosing regimen and formulations used in year 2 second dosing of this study. Twelve months after the first dose of pneumococcal vaccine, individuals in each conjugate cohort were re-randomized to receive either the same formulation as the first dose or 23vPS to assess the response to subsequent conjugate or polysaccharide vaccine. Individuals who initially received 23vPS received a dose of 7-valent pneumococcal conjugate vaccine (PREVNAR® (pneumococcal 7-valent conjugate vaccine [diphtheria CRM$_{197}$ protein])). A total of 314 subjects (out of 443) participated in the second year of the study.

Results after a Second Dose of Vaccine

Immune responses as well as safety and tolerability to a pneumococcal conjugate dose after an initial dose of either PnC or 23vPS when given 12 months after a first injection were assessed. Additionally, immune responses as well as safety and tolerability of 7vPnC and/or 23vPS when given after a prior dose of conjugate vaccine, were assessed. As in Example 1, blood samples were obtained from subjects prior to and one month post vaccination. Serotype specific antibody production and functional antibody responses were measured by ELISA and OPA analyses, respectively. Local and systemic reactions were assessed and recorded up to two weeks post vaccination dosing.

ELISA geometric mean antibody concentration (GMCs) results for each of 7 common serotypes following first and second vaccine doses are shown in Tables 7, 8, 9, and 10. The ELISA results for comparative treatment groups are shown in each of Table 7 (23vPS Dose 1 vs. 7vPnC Dose 1/23vPS Dose 2); Table 8 (7vPnC Dose 1 vs. 7vPnC Dose 1/7vPnC Dose 2); and Table 9 (7vPnC Dose 1 vs. 23vPS Dose 1/7vPnC Dose 2). Table 10 shows detailed immunogenicity results for each of the treatment groups.

TABLE 7

Pneumococcal ELISA Geometric Mean Antibody Concentrations (µg/mL) (Dose 1 and Dose 2 Evaluable Immunogenicity Populations)

| | Sampling Time$^a$ | | | | | |
|---|---|---|---|---|---|---|
| | 23vPS, Post-Dose 1 | | | 7vPnC/23vPS, Post-Dose 2 | | |
| Serotype | $N^b$ | GMC$^c$ | 95% CI$^d$ | $N^b$ | GMC$^c$ | 95% CI$^d$ |
| 4 | 62 | 1.6 | (1.1, 2.5) | 30 | 1.5 | (0.9, 2.6) |
| 6B | 62 | 4.4 | (3.2, 6.0) | 30 | 5.0 | (2.7, 9.1) |
| 9V | 62 | 3.4 | (2.5, 4.6) | 30 | 6.1 | (3.6, 10.3) |
| 14 | 62 | 8.9 | (5.3, 15.0) | 30 | 15.0 | (8.4, 26.8) |
| 18C | 62 | 6.6 | (4.6, 9.6) | 30 | 7.1 | (4.6, 10.9) |
| 19F | 62 | 4.5 | (3.1, 6.6) | 30 | 8.0 | (4.7, 13.8) |
| 23F | 62 | 3.8 | (2.6, 5.6) | 30 | 7.5 | (3.7, 15.1) |

$^a$Protocol specified timing for blood sample.
$^b$N = the number of subjects with assay results for the specified serotype and the given visit.
$^c$Geometric Mean Concentrations (GMCs) were calculated using all subjects with available data for the specified blood draw.
$^d$Confidence limits (CI) are back transforms of a confidence interval based on Student's t-distribution for the mean logarithm of the concentrations.

TABLE 8

Pneumococcal ELISA Geometric Mean Antibody Concentrations (µg/mL) (Dose 1 and Dose 2 Evaluable Immunogenicity Populations)

| | Sampling Time$^a$ | | | | | |
|---|---|---|---|---|---|---|
| | 7vPnC, Post-Dose 1 | | | 7vPnC/7vPnC, Post-Dose 2 | | |
| Serotype | $N^b$ | GMC$^c$ | 95% CI$^d$ | $N^b$ | GMC$^c$ | 95% CI$^d$ |
| 4 | 61 | 2.6 | (1.7, 4.0) | 31 | 3.3 | (1.9, 5.7) |
| 6B | 61 | 7.4 | (4.7, 11.8) | 31 | 8.3 | (4.1, 16.8) |
| 9V | 61 | 8.5 | (6.2, 11.8) | 31 | 6.6 | (4.5, 9.5) |
| 14 | 61 | 16.1 | (9.9, 26.1) | 31 | 17.6 | (10.2, 30.3) |

TABLE 8-continued

Pneumococcal ELISA Geometric Mean Antibody Concentrations
(μg/mL) (Dose 1 and Dose 2 Evaluable Immunogenicity Populations)

| | Sampling Time[a] | | | | | |
|---|---|---|---|---|---|---|
| | 7vPnC, Post-Dose 1 | | | 7vPnC/7vPnC, Post-Dose 2 | | |
| Serotype | N[b] | GMC[c] | 95% CI[d] | N[b] | GMC[c] | 95% CI[d] |
| 18C | 61 | 11.4 | (8.4, 15.5) | 31 | 10.0 | (7.2, 13.8) |
| 19F | 61 | 5.6 | (3.9, 8.2) | 31 | 6.7 | (3.9, 11.3) |
| 23F | 61 | 12.5 | (8.1, 19.4) | 31 | 16.5 | (11.5, 23.7) |

[a]Protocol specified timing for blood sample.
[b]N = the number of subjects with assay results for the specified serotype and the given visit.
[c]Geometric Mean Concentrations (GMCs) were calculated using all subjects with available data for the specified blood draw.
[d]Confidence limits (CI) are back transforms of a confidence interval based on Student's t-distribution for the mean logarithm of the concentrations.

Treatment group 7vPnC/23vPS: The point estimates for ELISA GMCs for a subsequent dose of 23vPS following 7vPnC were higher than after an initial dose of 23vPS alone for all but one (serotype 4) of the common serotypes. See Table 7.

Treatment group 7vPnC/7vPnC: The point estimates for ELISA GMCs after a second dose of 7vPnC were higher than after an initial dose of 23vPS. The ELISA GMC's for a subsequent dose of 7vPnC following 7vPnC were similar to an initial dose of 7vPnC. See Table 3 above for the 23vPS results as comparison. See Table 8.

TABLE 9

Pneumococcal ELISA Geometric Mean Antibody Concentrations
(μg/mL) (Dose 1 and Dose 2 Evaluable Immunogenicity Populations)

| | Sampling Time[a] | | | | | |
|---|---|---|---|---|---|---|
| | 7vPnC, Post-Dose 1 | | | 23vPS/7vPnC, Post-Dose 2 | | |
| Serotype | N[b] | GMC[c] | 95% CI[d] | N[b] | GMC[c] | 95% CI[d] |
| 4 | 61 | 2.6 | (1.7, 4.0) | 62 | 1.0 | (0.6, 1.5) |
| 6B | 61 | 7.4 | (4.7, 11.8) | 62 | 2.7 | (1.9, 4.0) |
| 9V | 61 | 8.5 | (6.2, 11.8) | 62 | 2.8 | (2.0, 3.9) |
| 14 | 61 | 16.1 | (9.9, 26.1) | 62 | 6.9 | (4.2, 11.1) |
| 18C | 61 | 11.4 | (8.4, 15.5) | 62 | 5.2 | (3.8, 7.3) |
| 19F | 61 | 5.6 | (3.9, 8.2) | 62 | 2.2 | (1.5, 3.3) |
| 23F | 61 | 12.5 | (8.1, 19.4) | 62 | 3.7 | (2.3, 6.2) |

[a]Protocol specified timing for blood sample.
[b]N = the number of subjects with assay results for the specified serotype and the given visit.
[c]Geometric Mean Concentrations (GMCs) were calculated using all subjects with available data for the specified blood draw.
[d]Confidence limits (CI) are back transforms of a confidence interval based on Student's t-distribution for the mean logarithm of the concentrations.

Treatment group 23vPnC/7vPnC: The point estimates for ELISA GMCs for a subsequent dose of 7vPnC following 23vPS were lower than after an initial dose of 7vPnC for all serotypes and are statistically inferior for 6 of the 7 serotypes. These data showed induction of hyporesponsiveness after a single dose of 23vPS vaccine. See Table 9.

Functional antibody response as measured by OPA analyses for each of the seven common serotypes 4, 6B, 9V, 14, 18C, 19F and 23F, following a single dose of vaccine or a second dose of vaccine are shown in Table 11.

TABLE 10

Pneumococcal ELISA Geometric Mean Antibody Concentrations (μg/mL) (Dose 1 and Dose 2 Evaluable Immunogenicity Populations)

| Sero-type | Randomized Treatment (Dose 1/Dose 2) | Sampling Time[a] | | | | | | | | | | | |
|---|---|---|---|---|---|---|---|---|---|---|---|---|---|
| | | Pre-Dose 1 | | | Post-Dose 1 | | | Pre-Dose 2 | | | Post-Dose 2 | | |
| | | N[b] | GMC[c] | 95% CI[d] | N[b] | GMC[c] | 95% CI[d] | N[b] | GMC[c] | 95% CI[d] | N[b] | GMC[c] | 95% CI[d] |
| 4 | 7vPnC | 61 | 0.2 | (0.1, 0.3) | 61 | 2.6 | (1.7, 4.0) | | | | | | |
| | 23vPS | 62 | 0.2 | (0.1, 0.3) | 62 | 1.6 | (1.1, 2.5) | | | | | | |
| | 7vPnC/23vPS | | | | | | | 30 | 0.7 | (0.4, 1.2) | 30 | 1.5 | (0.9, 2.6) |
| | 7vPnC/7vPnC | | | | | | | 31 | 0.9 | (0.4, 1.7) | 31 | 3.3 | (1.9, 5.7) |
| | 23vPS/7vPnC | | | | | | | 62 | 0.5 | (0.3, 0.8) | 62 | 1.0 | (0.6, 1.5) |
| 6B | 7vPnC | 61 | 1.1 | (0.8, 1.7) | 61 | 7.4 | (4.7, 11.8) | | | | | | |
| | 23vPS | 62 | 1.0 | (0.7, 1.4) | 62 | 4.4 | (3.2, 6.0) | | | | | | |
| | 7vPnC/23vPS | | | | | | | 30 | 2.0 | (1.1, 3.7) | 30 | 5.0 | (2.7, 9.1) |
| | 7vPnC/7vPnC | | | | | | | 31 | 2.3 | (1.2, 4.5) | 31 | 8.3 | (4.1, 16.8) |
| | 23vPS/7vPnC | | | | | | | 62 | 1.5 | (1.0, 2.1) | 62 | 2.7 | (1.9, 4.0) |
| 9V | 7vPnC | 61 | 0.9 | (0.7, 1.3) | 61 | 8.5 | (6.2, 11.8) | | | | | | |
| | 23vPS | 62 | 0.7 | (0.5, 1.0) | 62 | 3.4 | (2.5, 4.6) | | | | | | |
| | 7vPnC/23vPS | | | | | | | 30 | 3.9 | (2.3, 6.7) | 30 | 6.1 | (3.6, 10.3) |
| | 7vPnC/7vPnC | | | | | | | 31 | 3.3 | (2.0, 5.4) | 31 | 6.6 | (4.5, 9.5) |
| | 23vPS/7vPnC | | | | | | | 62 | 1.4 | (1.0, 2.0) | 62 | 2.8 | (2.0, 3.9) |
| 14 | 7vPnC | 61 | 2.8 | (1.7, 4.5) | 61 | 16.1 | (9.9, 26.1) | | | | | | |
| | 23vPS | 62 | 1.6 | (1.0, 2.4) | 62 | 8.9 | (5.3, 15.0) | | | | | | |
| | 7vPnC/23vPS | | | | | | | 30 | 7.8 | (3.8, 16.4) | 30 | 15.0 | (8.4, 26.8) |
| | 7vPnC/7vPnC | | | | | | | 31 | 10.5 | (5.1, 21.7) | 31 | 17.6 | (10.2, 30.3) |
| | 23vPS/7vPnC | | | | | | | 62 | 5.5 | (3.3, 9.2) | 62 | 6.9 | (4.2, 11.1) |
| 18C | 7vPnC | 61 | 1.2 | (0.9, 1.6) | 61 | 11.4 | (8.4, 15.5) | | | | | | |
| | 23vPS | 62 | 1.0 | (0.7, 1.4) | 62 | 6.6 | (4.6, 9.6) | | | | | | |
| | 7vPnC/23vPS | | | | | | | 30 | 5.0 | (3.0, 8.5) | 30 | 7.1 | (4.6, 10.9) |
| | 7vPnC/7vPnC | | | | | | | 31 | 5.6 | (3.6, 8.6) | 31 | 10.0 | (7.2, 13.8) |
| | 23vPS/7vPnC | | | | | | | 62 | 3.2 | (2.2, 4.7) | 62 | 5.2 | (3.8, 7.3) |
| 19F | 7vPnC | 61 | 1.4 | (0.9, 2.0) | 61 | 5.6 | (3.9, 8.2) | | | | | | |
| | 23vPS | 62 | 1.1 | (0.8, 1.5) | 62 | 4.5 | (3.1, 6.6) | | | | | | |
| | 7vPnC/23vPS | | | | | | | 30 | 2.8 | (1.6, 4.9) | 30 | 8.0 | (4.7, 13.8) |
| | 7vPnC/7vPnC | | | | | | | 31 | 1.6 | (0.9, 3.0) | 31 | 6.7 | (3.9, 11.3) |
| | 23vPS/7vPnC | | | | | | | 62 | 1.5 | (1.0, 2.3) | 62 | 2.2 | (1.5, 3.3) |
| 23F | 7vPnC | 61 | 1.1 | (0.8, 1.5) | 61 | 12.5 | (8.1, 19.4) | | | | | | |
| | 23vPS | 62 | 0.9 | (0.6, 1.3) | 62 | 3.8 | (2.6, 5.6) | | | | | | |

TABLE 10-continued

Pneumococcal ELISA Geometric Mean Antibody Concentrations (μg/mL) (Dose 1 and Dose 2 Evaluable Immunogenicity Populations)

| Sero-type | Randomized Treatment (Dose 1/Dose 2) | Sampling Time[a] | | | | | | | | | | |
|---|---|---|---|---|---|---|---|---|---|---|---|---|
| | | Pre-Dose 1 | | | Post-Dose 1 | | | Pre-Dose 2 | | | Post-Dose 2 | |
| | | N[b] | GMC[c] | 95% CI[d] | N[b] | GMC[c] | 95% CI[d] | N[b] | GMC[c] | 95% CI[d] | N[b] | GMC[c] | 95% CI[d] |
| | 7vPnC/23vPS | | | | | | | 30 | 6.1 | (2.8, 13.1) | 30 | 7.5 | (3.7, 15.1) |
| | 7vPnC/7vPnC | | | | | | | 31 | 3.8 | (2.1, 6.6) | 31 | 16.5 | (11.5, 23.7) |
| | 23vPS/7vPnC | | | | | | | 62 | 1.4 | (0.9, 2.1) | 62 | 3.7 | (2.3, 6.2) |

[a]Protocol specified timing for blood sample.
[b]N = the number of subjects with assay results for the specified serotype and the given visit.
[c]Geometric Mean Concentrations (GMCs) were calculated using all subjects with available data for the specified blood draw.
[d]Confidence limits (CI) are back transforms of a confidence interval based on Student's t-distribution for the mean logarithm of the concentrations.

TABLE 11

Pneumococcal OPA Geometric Mean Antibody Titers for Dose 2 (Evaluable Immunogenicity Population)

| Serotype | Randomized Treatment Group (Dose 1/Dose 2) | Sampling Time[a] | | | | | | | | |
|---|---|---|---|---|---|---|---|---|---|---|
| | | Pre-Dose 2 | | | 1 Month Post-Dose 2 | | | Fold Rise (Post/Pre) | | |
| | | N[b] | GMT[c] | 95% CI[d] | N[b] | GMT[c] | 95% CI[d] | N[b] | GMFR[e] | 95% CI[d] |
| 1 | 7vPnC/23vPS | 30 | 5.2 | (4.1, 6.6) | 30 | 90.5 | (46.4, 176.6) | 30 | 17.5 | (9.4, 32.9) |
| | 7vPnC/7vPnC | 33 | 7.2 | (5.1, 10.2) | 33 | 6.3 | (4.5, 8.9) | 33 | 0.9 | (0.7, 1.2) |
| | 2x/23vPS | 33 | 24.9 | (14.9, 41.4) | 32 | 94.5 | (51.8, 172.6) | 32 | 4.0 | (2.4, 6.7) |
| | 2x/2x | 36 | 33.3 | (18.0, 61.6) | 36 | 109.7 | (58.9, 204.4) | 36 | 3.3 | (2.0, 5.5) |
| | 4x/23vPS | 30 | 36.8 | (19.4, 69.6) | 30 | 82.5 | (48.9, 139.4) | 30 | 2.2 | (1.3, 3.8) |
| | 4x/4x | 33 | 30.7 | (17.2, 54.6) | 33 | 168.2 | (90.2, 313.7) | 33 | 5.5 | (3.1, 9.7) |
| | 23vPS/7vPnC | 63 | 16.4 | (11.1, 24.2) | 63 | 15.7 | (10.6, 23.0) | 63 | 1.0 | (0.8, 1.2) |
| 4 | 7vPnC/23vPS | 30 | 330.1 | (140.3, 776.7) | 30 | 1203.8 | (646.4, 2241.7) | 30 | 3.6 | (1.9, 7.1) |
| | 7vPnC/7vPnC | 33 | 397.9 | (185.7, 852.6) | 33 | 1433.0 | (935.7, 2194.7) | 33 | 3.6 | (1.8, 7.2) |
| | 2x/23vPS | 33 | 235.4 | (107.7, 514.2) | 32 | 1046.4 | (636.1, 1721.3) | 32 | 4.7 | (2.5, 8.7) |
| | 2x/2x | 36 | 456.1 | (238.1, 873.9) | 36 | 1149.4 | (653.4, 2021.9) | 36 | 2.5 | (1.6, 4.0) |
| | 4x/23vPS | 30 | 574.7 | (321.4, 1027.5) | 30 | 851.2 | (465.3, 1557.0) | 30 | 1.5 | (1.1, 2.1) |
| | 4x/4x | 33 | 480.7 | (276.2, 836.8) | 33 | 1922.9 | (1277.1, 2895.4) | 33 | 4.0 | (2.5, 6.3) |
| | 23vPS/7vPnC | 63 | 210.0 | (128.5, 343.2) | 63 | 506.4 | (349.7, 733.4) | 63 | 2.4 | (1.7, 3.5) |
| 5 | 7vPnC/23vPS | 30 | 8.4 | (5.1, 13.8) | 30 | 150.5 | (81.4, 278.1) | 30 | 18.0 | (9.0, 35.9) |
| | 7vPnC/7vPnC | 33 | 9.5 | (5.1, 17.6) | 33 | 7.5 | (4.8, 11.9) | 33 | 0.8 | (0.5, 1.2) |
| | 2x/23vPS | 33 | 39.5 | (19.6, 79.7) | 32 | 162.4 | (90.9, 290.2) | 32 | 4.5 | (2.6, 7.6) |
| | 2x/2x | 36 | 48.9 | (25.2, 94.9) | 36 | 130.5 | (66.7, 255.4) | 36 | 2.7 | (1.6, 4.4) |
| | 4x/23vPS | 30 | 59.7 | (25.7, 138.6) | 30 | 189.6 | (105.8, 339.8) | 30 | 3.2 | (1.7, 5.9) |
| | 4x/4x | 32 | 39.7 | (18.3, 86.3) | 33 | 261.4 | (142.5, 479.6) | 32 | 6.3 | (3.6, 11.0) |
| | 23vPS/7vPnC | 62 | 55.3 | (32.9, 93.0) | 63 | 62.6 | (38.4, 102.1) | 62 | 1.2 | (0.9, 1.6) |
| 6B | 7vPnC/23vPS | 30 | 157.6 | (53.3, 465.7) | 30 | 1072.4 | (460.2, 2499.2) | 30 | 6.8 | (3.2, 14.5) |
| | 7vPnC/7vPnC | 33 | 284.3 | (110.2, 733.9) | 33 | 2323.1 | (1207.3, 4469.9) | 33 | 8.2 | (3.5, 18.9) |
| | 2x/23vPS | 33 | 461.0 | (178.2, 1192.1) | 33 | 941.5 | (450.7, 1966.8) | 33 | 2.0 | (1.1, 3.7) |
| | 2x/2x | 36 | 261.0 | (98.3, 693.0) | 36 | 2298.8 | (1045.5, 5054.4) | 36 | 8.8 | (3.8, 20.5) |
| | 4x/23vPS | 30 | 500.3 | (186.6, 1341.2) | 30 | 691.4 | (308.7, 1548.3) | 30 | 1.4 | (0.7, 2.7) |
| | 4x/4x | 32 | 459.4 | (179.9, 1173.2) | 33 | 3052.5 | (1743.8, 5343.3) | 32 | 6.7 | (2.9, 15.7) |
| | 23vPS/7vPnC | 63 | 186.1 | (104.0, 332.8) | 63 | 438.9 | (248.9, 774.1) | 63 | 2.4 | (1.4, 4.0) |
| 9V | 7vPnC/23vPS | 30 | 1047.9 | (576.1, 1906.2) | 30 | 2144.9 | (1006.4, 4571.1) | 30 | 2.0 | (0.9, 4.9) |
| | 7vPnC/7vPnC | 33 | 902.7 | (434.7, 1874.8) | 33 | 2274.8 | (1277.7, 4049.9) | 33 | 2.5 | (1.5, 4.4) |
| | 2x/23vPS | 33 | 1045.7 | (538.8, 2029.7) | 33 | 2323.1 | (1139.3, 4736.8) | 33 | 2.2 | (1.2, 4.0) |
| | 2x/2x | 36 | 844.7 | (420.7, 1696.0) | 36 | 3128.2 | (1704.6, 5740.7) | 36 | 3.7 | (2.1, 6.5) |
| | 4x/23vPS | 30 | 2001.2 | (1312.7, 3050.8) | 30 | 2702.4 | (1385.5, 5270.8) | 30 | 1.4 | (0.7, 2.6) |
| | 4x/4x | 32 | 1191.7 | (666.6, 2130.1) | 33 | 4010.9 | (2614.7, 6152.5) | 32 | 3.4 | (2.2, 5.1) |
| | 23vPS/7vPnC | 63 | 463.7 | (267.5, 803.9) | 63 | 1290.2 | (792.2, 2101.2) | 63 | 2.8 | (1.8, 4.3) |
| 14 | 7vPnC/23vPS | 29 | 976.2 | (415.5, 2293.5) | 30 | 2521.4 | (1308.4, 4859.0) | 29 | 2.5 | (1.3, 5.1) |
| | 7vPnC/7vPnC | 33 | 1433.0 | (730.8, 2810.1) | 33 | 3183.4 | (1948.6, 5200.8) | 33 | 2.2 | (1.3, 3.8) |
| | 2x/23vPS | 33 | 1137.4 | (649.6, 1991.6) | 33 | 2048.0 | (1150.8, 3644.7) | 33 | 1.8 | (1.0, 3.4) |
| | 2x/2x | 35 | 1108.4 | (549.3, 2236.6) | 36 | 1689.3 | (946.9, 3013.8) | 35 | 1.5 | (0.8, 2.7) |
| | 4x/23vPS | 30 | 1123.1 | (583.7, 2161.2) | 30 | 2001.2 | (1234.7, 3243.7) | 30 | 1.8 | (1.1, 3.0) |
| | 4x/4x | 32 | 1357.0 | (728.9, 2526.4) | 33 | 2580.3 | (1645.1, 4047.3) | 32 | 1.9 | (1.0, 3.6) |
| | 23vPS/7vPnC | 63 | 652.2 | (369.3, 1151.9) | 63 | 1221.1 | (781.2, 1908.7) | 63 | 1.9 | (1.4, 2.5) |
| 18C | 7vPnC/23vPS | 30 | 280.8 | (126.5, 623.5) | 30 | 955.4 | (549.2, 1662.1) | 30 | 3.4 | (2.0, 5.7) |
| | 7vPnC/7vPnC | 33 | 397.9 | (204.8, 773.1) | 33 | 1067.9 | (648.4, 1758.9) | 33 | 2.7 | (1.7, 4.2) |
| | 2x/23vPS | 33 | 203.2 | (95.1, 434.1) | 33 | 593.1 | (301.1, 1168.4) | 33 | 2.9 | (1.7, 5.0) |
| | 2x/2x | 36 | 438.9 | (218.8, 880.3) | 36 | 844.7 | (480.0, 1486.3) | 36 | 1.9 | (1.2, 3.1) |
| | 4x/23vPS | 30 | 445.7 | (243.2, 816.8) | 30 | 645.1 | (354.8, 1172.7) | 30 | 1.4 | (1.0, 2.1) |
| | 4x/4x | 32 | 534.7 | (245.1, 1166.2) | 33 | 1237.1 | (637.8, 2399.6) | 32 | 2.4 | (1.3, 4.2) |
| | 23vPS/7vPnC | 63 | 196.6 | (115.0, 336.1) | 63 | 312.1 | (190.2, 512.0) | 63 | 1.6 | (1.2, 2.1) |

TABLE 11-continued

Pneumococcal OPA Geometric Mean Antibody Titers for Dose 2 (Evaluable Immunogenicity Population)

| | Randomized Treatment Group | Sampling Time[a] | | | | | | | | |
|---|---|---|---|---|---|---|---|---|---|---|
| | | Pre-Dose 2 | | | 1 Month Post-Dose 2 | | | Fold Rise (Post/Pre) | | |
| Serotype | (Dose 1/Dose 2) | N[b] | GMT[c] | 95% CI[d] | N[b] | GMT[c] | 95% CI[d] | N[b] | GMFR[e] | 95% CI[d] |
| 19F | 7vPnC/23vPS | 30 | 71.8 | (31.2, 165.2) | 30 | 435.5 | (244.0, 777.5) | 30 | 6.1 | (2.5, 14.5) |
| | 7vPnC/7vPnC | 33 | 37.9 | (18.2, 78.7) | 33 | 284.3 | (147.5, 548.2) | 33 | 7.5 | (4.3, 13.0) |
| | 2x/23vPS | 33 | 60.1 | (25.1, 144.0) | 33 | 261.4 | (144.8, 472.1) | 33 | 4.4 | (2.2, 8.6) |
| | 2x/2x | 36 | 52.8 | (25.7, 108.6) | 36 | 237.0 | (121.9, 461.0) | 36 | 4.5 | (2.3, 8.7) |
| | 4x/23vPS | 30 | 50.8 | (19.3, 133.9) | 30 | 406.4 | (190.4, 867.1) | 30 | 8.0 | (3.9, 16.4) |
| | 4x/4x | 32 | 64.0 | (29.6, 138.2) | 33 | 250.7 | (126.3, 497.6) | 32 | 3.8 | (1.9, 7.5) |
| | 23vPS/7vPnC | 63 | 61.2 | (32.8, 114.4) | 63 | 114.7 | (65.4, 201.1) | 63 | 1.9 | (1.2, 2.9) |
| 23F | 7vPnC/23vPS | 30 | 601.9 | (265.7, 1363.3) | 30 | 1290.2 | (612.1, 2719.3) | 30 | 2.1 | (1.2, 3.8) |
| | 7vPnC/7vPnC | 33 | 605.7 | (235.2, 1559.9) | 33 | 4948.3 | (2650.2, 9239.4) | 33 | 8.2 | (3.8, 17.5) |
| | 2x/23vPS | 33 | 284.3 | (112.4, 719.3) | 33 | 631.7 | (281.2, 1419.0) | 33 | 2.2 | (1.2, 4.3) |
| | 2x/2x | 35 | 403.7 | (169.1, 963.6) | 36 | 1722.2 | (723.4, 4099.9) | 35 | 4.2 | (2.0, 8.6) |
| | 4x/23vPS | 30 | 488.9 | (197.4, 1210.5) | 30 | 831.7 | (337.4, 2050.1) | 30 | 1.7 | (1.0, 2.8) |
| | 4x/4x | 32 | 789.6 | (392.0, 1590.7) | 33 | 5496.3 | (3414.4, 8847.6) | 32 | 6.9 | (3.3, 14.4) |
| | 23vPS/7vPnC | 62 | 88.5 | (46.4, 168.9) | 63 | 458.7 | (225.7, 931.9) | 62 | 5.5 | (2.9, 10.5) |

[a]Protocol specified timing for blood sample.
[b]N = Number of subjects with assay results for the specified serotype and the given visit.
[c]Geometric Mean Titers (GMTs) were calculated using all subjects with available data for the specified blood draw.
[d]Confidence limits (CI) are back transforms of a confidence interval based on Student's t-distribution for the mean logarithm of the concentrations or fold-rises.
[e]Geometric Mean Fold Rises (GMFRs) were calculated using all subjects with available data from both the pre-dose and post-dose blood draws.
2x = 9vPnC reconstituted with 7vPnC.
4x = 2 doses 9vPnC reconstituted with 2 doses 7vPnC.

After an initial 7vPnC vaccine dose, geometric mean titers (GMTs) of six out of seven serotypes assessed, were superior as compared to an initial dose of 23vPS vaccine. 7vPnC/23vPS recipients had higher GMTs (point estimates) compared to 23vPS alone. 19F was the only serotype which did not demonstrate superior activity response, however, the results did not demonstrate activity of 19F serotype response to be inferior to other treatment groups. See Table 11. In contrast, treatment group 23vPS/7vPnC recipients, receiving a second dose of 7vPnC following an initial dose of 23vPS vaccine yielded lower GMTs as compared to 7vPnC alone for each of the serotypes assessed. See Table 11.

The collection period for local and systemic reactogenicity after dose 1 was 7 days. The protocol was amended to extend the collection period up to 14 days after dose 2. See Table 12 and Table 13 for a summary of the results from dose 2. There were no serious adverse events that were assessed to be vaccine related.

Pain at the injection site and redness were the most frequently observed local reactions after dose 1 and 2. Following dose 1, pain at the injection site and redness were comparable between the 7vPnC and 23vPS groups with a trend toward higher responses in the 7vPnC group. Following dose 2, more individuals reported pain and redness at the injection site after polysaccharide following 7vPnC vaccine than after polysaccharide vaccine alone. See Table 12.

The incidences of any systemic reactions were comparable between 7vPnC vaccine and 23vPS vaccine after a single dose as shown in Example 1. Systemic reactions were higher (except fever) when 23vPS was given after 7vPnC as compared to a single dose of either individual vaccine. Fever was rare with a total of 9 cases after dose 1 and 9 cases after dose 2. After dose 1 all 9 cases were between 38° C. and 39° C. (1 after 7vPnC, 2 after 2×PnC, 3 after 4×PnC, 3 after 23vPS). After dose 2, 8 cases were between 38° C. and 39° C. (3 after 7vPnC/23vPS, 2 after 2×/2×, 3 after 23vPS/7vPnC), 1 case of fever >39° C. after 7vPnC/23vPS and none over 40° C. See Table 13.

TABLE 12

Percent of Subjects Reporting Injection Site Events Within 14 Days Following Dose 2

| | Actual Treatment Group (Dose 1/Dose 2) | | | | | | | | | | | | | |
|---|---|---|---|---|---|---|---|---|---|---|---|---|---|---|
| | 7vPnC/ 23vPS | | 7vPnC/ 7vPnC | | 2x/23vPS | | 2x/2x | | 4x/23vPS | | 4x/4x | | 23vPS/ 7vPnC | | p-value[b] |
| | N[a] | % | N[a] | % | N[a] | % | N[a] | % | N[a] | % | N[a] | % | N[a] | % | |
| Redness | | | | | | | | | | | | | | | |
| Any | 37 | 45.9 | 37 | 24.3 | 34 | 52.9 | 35 | 25.7 | 33 | 39.4 | 39 | 64.1 | 72 | 30.6 | 0.001 |
| Significant[c] | 34 | 17.6 | 36 | 11.1 | 32 | 34.4 | 35 | 14.3 | 31 | 22.6 | 36 | 41.7 | 68 | 10.3 | 0.002 |
| >7 cm[d] | 33 | 3.0 | 35 | 5.7 | 32 | 12.5 | 35 | 2.9 | 30 | 3.3 | 34 | 2.9 | 66 | 1.5 | 0.331 |
| Swelling | | | | | | | | | | | | | | | |
| Any | 36 | 36.1 | 35 | 28.6 | 36 | 47.2 | 36 | 25.0 | 33 | 27.3 | 38 | 44.7 | 70 | 27.1 | 0.204 |
| Significant[c] | 34 | 14.7 | 34 | 14.7 | 32 | 34.4 | 36 | 11.1 | 32 | 12.5 | 37 | 35.1 | 67 | 7.5 | 0.003 |
| >7 cm[d] | 32 | 3.1 | 34 | 8.8 | 31 | 9.7 | 36 | 0.0 | 32 | 3.1 | 35 | 2.9 | 65 | 0.0 | 0.047 |

TABLE 12-continued

Percent of Subjects Reporting Injection Site Events Within 14 Days Following Dose 2

| | Actual Treatment Group (Dose 1/Dose 2) | | | | | | | | | | | | | |
|---|---|---|---|---|---|---|---|---|---|---|---|---|---|---|
| | 7vPnC/ 23vPS | | 7vPnC/ 7vPnC | | 2x/23vPS | | 2x/2x | | 4x/23vPS | | 4x/4x | | 23vPS/ 7vPnC | | p- |
| | $N^a$ | % | $N^a$ | % | $N^a$ | % | $N^a$ | % | $N^a$ | % | $N^a$ | % | $N^a$ | % | value$^b$ |
| Pain at injection site | | | | | | | | | | | | | | | |
| Any | 38 | 52.6 | 38 | 42.1 | 36 | 58.3 | 37 | 43.2 | 32 | 40.6 | 40 | 57.5 | 71 | 26.8 | 0.012 |
| Significant$^e$ | 37 | 18.9 | 37 | 8.1 | 33 | 27.3 | 36 | 5.6 | 32 | 15.6 | 37 | 13.5 | 70 | 0.0 | <.001 |
| Any Injection Site Reaction$^f$ | 37 | 67.6 | 36 | 52.8 | 36 | 77.8 | 37 | 56.8 | 32 | 65.6 | 39 | 84.6 | 71 | 49.3 | 0.002 |

$^a$N represents the number of subjects with known values.
$^b$Fisher Exact test, two-sided, for percent of subjects among all treatment groups.
$^c$Significant was defined as having a diameter for the involved area >8 caliper units or 4.0 cm, including subjects with local reactions >7.0 cm.
$^d$For comparability with Dose 2, since subjects with local reactions >7.0 cm at Dose 1 were encouraged not to return for Dose 2.
$^e$Significant was defined as interfering with limb movement.
$^f$Any injection site reaction includes any pain, any swelling, and any redness. Subjects were included in this category if they experienced an event or had 'no' for all days for all events (i.e., any missing value excludes the subject unless they experienced an event).
2x = 9vPnC reconstituted with 7vPnC.
4x = 2 doses 9vPnC reconstituted with 2 doses 7vPnC.

TABLE 13

Percent of Subjects Reporting Systemic Reactions Within 14 Days Following Dose 2

| | Actual Treatment Group (Dose 1/Dose 2) | | | | | | | | | | | | | |
|---|---|---|---|---|---|---|---|---|---|---|---|---|---|---|
| Systemic | 7vPnC/ 23vPS | | 7vPnC/ 7vPnC | | 2x/23vPS | | 2x/2x | | 4x/23vPS | | 4x/4x | | 23vPS/ 7vPnC | | p- |
| Reaction | $N^a$ | % | $N^a$ | % | $N^a$ | % | $N^a$ | % | $N^a$ | % | $N^a$ | % | $N^a$ | % | value$^b$ |
| Fever ≥38° C. | 36 | 8.3 | 38 | 0.0 | 34 | 0.0 | 35 | 5.7 | 34 | 0.0 | 38 | 0.0 | 68 | 5.9 | 0.112 |
| Fever >39° C. | 36 | 2.8 | 38 | 0.0 | 34 | 0.0 | 35 | 0.0 | 34 | 0.0 | 38 | 0.0 | 68 | 0.0 | 0.493 |
| Fever >40° C. | 36 | 0.0 | 38 | 0.0 | 34 | 0.0 | 35 | 0.0 | 34 | 0.0 | 38 | 0.0 | 68 | 0.0 | >.999 |
| Fatigue | 38 | 42.1 | 40 | 25.0 | 35 | 37.1 | 36 | 27.8 | 34 | 5.9 | 39 | 17.9 | 71 | 28.2 | 0.009 |
| Headache | 38 | 23.7 | 40 | 12.5 | 36 | 19.4 | 36 | 16.7 | 34 | 2.9 | 39 | 7.7 | 72 | 16.7 | 0.147 |
| Chills | 37 | 18.9 | 39 | 10.3 | 34 | 5.9 | 36 | 5.6 | 34 | 5.9 | 40 | 7.5 | 71 | 7.0 | 0.492 |
| Rash | 36 | 2.8 | 39 | 0.0 | 34 | 2.9 | 36 | 2.8 | 33 | 3.0 | 38 | 2.6 | 70 | 1.4 | 0.911 |
| Vomiting | 36 | 0.0 | 38 | 0.0 | 35 | 5.7 | 36 | 2.8 | 34 | 2.9 | 39 | 0.0 | 70 | 1.4 | 0.348 |
| Decreased appetite | 36 | 8.3 | 38 | 7.9 | 34 | 8.8 | 36 | 8.3 | 34 | 8.8 | 39 | 12.8 | 70 | 11.4 | >.999 |
| Joint pain | 37 | 16.2 | 38 | 26.3 | 35 | 20.0 | 36 | 13.9 | 33 | 27.3 | 40 | 20.0 | 69 | 15.9 | 0.689 |
| Aggravated joint pain | 28 | 10.7 | 31 | 19.4 | 31 | 16.1 | 26 | 7.7 | 27 | 18.5 | 35 | 14.3 | 57 | 14.0 | 0.893 |
| New joint pain | 28 | 7.1 | 30 | 6.7 | 31 | 16.1 | 27 | 3.7 | 28 | 10.7 | 36 | 16.7 | 59 | 3.4 | 0.211 |
| Muscle pain | 38 | 34.2 | 38 | 21.1 | 36 | 38.9 | 37 | 18.9 | 31 | 25.8 | 40 | 25.0 | 73 | 20.5 | 0.338 |
| Aggravated muscle pain | 31 | 12.9 | 30 | 6.7 | 33 | 12.1 | 26 | 3.8 | 26 | 7.7 | 32 | 6.3 | 55 | 7.3 | 0.885 |
| New muscle pain | 31 | 22.6 | 32 | 15.6 | 33 | 33.3 | 30 | 16.7 | 29 | 34.5 | 36 | 22.2 | 61 | 13.1 | 0.165 |
| Medication to treat fever | 33 | 3.0 | 37 | 0.0 | 31 | 0.0 | 33 | 6.1 | 28 | 0.0 | 33 | 3.0 | 61 | 1.6 | 0.568 |
| Any new medications | 33 | 12.1 | 35 | 2.9 | 30 | 6.7 | 32 | 6.3 | 26 | 7.7 | 32 | 12.5 | 52 | 5.8 | 0.738 |
| Any systemic reaction$^c$ | 37 | 67.6 | 36 | 55.6 | 36 | 61.1 | 33 | 45.5 | 29 | 69.0 | 35 | 42.9 | 63 | 55.6 | 0.221 |

$^a$N represents the number of subjects with known values.
$^b$Fisher Exact test, two-sided, for percent of subjects among all treatment groups.
$^c$Any systemic reaction excludes any new medications and any medications to treat a fever. Subjects were included in this category if they experienced an event or had 'no' for all days for all events (i.e., any missing value excludes the subject unless they experienced an event).
2x = 9vPnC reconstituted with 7vPnC.
4x = 2 doses 9vPnC reconstituted with 2 doses 7vPnC.

Summary of Study Results

This study demonstrated that conjugate pneumococcal vaccine induced a vigorous immune response for all vaccine serotypes after dose 1. Antibody levels were superior for all conjugate serotypes (except 19F, which was non-inferior) relative to unconjugated polysaccharide vaccine. Functional antibody activity in subjects receiving conjugate vaccine was also superior to that induced by polysaccharide vaccine after dose 1. Safety and tolerability were comparable between conjugate and polysaccharide.

To assess whether an earlier dose of conjugate vaccine could complement a subsequent dose of polysaccharide (7vPnC/23vPS), antibody responses after a second polysaccharide vaccine dose were compared to antibody levels after a single dose of polysaccharide vaccine (standard of care). For all common serotypes (except serotype 4), antibody levels trended higher than after polysaccharide alone. For all common serotypes, functional antibody activity resulted higher levels than after unconjugated polysaccharide vaccine alone. This suggests that conjugate vaccine improved the response to a subsequent dose of polysaccharide vaccine.

By contrast, individuals who were vaccinated with unconjugated polysaccharide first, before receiving conjugate (23vPS/7vPnC), had lower antibody levels after the subsequent conjugate compared to a single dose of conjugate. These observations support previous data indicating that the 23vPS vaccine may induce hyporesponsiveness.

The antibody response to a second dose of conjugate (7vPnC/7vPnC) trended higher than after a single dose of unconjugated polysaccharide for the majority of serotypes. Compared to the initial dose of conjugate, the immune response after the subsequent dose of conjugate vaccine was similar.

Local and systemic reactogenicity was comparable between conjugate and unconjugated polysaccharide after dose 1, with a trend toward higher responses in the 7vPnC group. A subsequent dose of polysaccharide increased local and systemic reactogenicity (except fever) relative to a single dose of conjugate or unconjugated polysaccharide. However, the majority of adverse events were non serious and were of short duration. There were no vaccine-related serious adverse events. The overall safety profile was acceptable.

Example 3

Comparison of Activity Levels of Pneumococcal Antibodies in Older Adult and Infant Populations Conjugate vaccine has been shown to significantly decrease pneumococcal pneumonia in three separate studies in infants. (S. Black, et al, *Eur J Pediatr.* 161 Suppl 2:S127-31. 2002; K. Klugman, et al, *N Engl J Med.* 349:1341-8. 2003; and F. Cutts, et al, *Lancet.* 365:1139-46, 2005.) The current 23vPs vaccine does not protect against community acquired pneumococcal pneumonia (CAP) in elderly adults. Antibody responses obtained in older adult populations described in Examples 1 and 2 above were compared to responses in infants after three doses of 7vPnC at two, four, and six months. The results are shown in Table 14.

The antibody response to a single dose of conjugate (7vPnC) in older adults induced OPA levels similar to those of infants after three doses of 7vPnC. See Table 14. In contrast, immunization with unconjugated polysaccharide induced increased levels of IgG antibodies, but the magnitude of the OPA titer is significantly lower than those achieved after immunization with 7vPnC. See Table 14. These results support conjugate vaccine achieved levels which may be able to induce protection in the elderly against pneumococcal pneumonia.

TABLE 14

Pneumococcal Antibody Levels in Elderly Subjects immunized with one dose of 7 Valent PnC or 23 valent Ps vs. Infants Immunized with 3 doses of 7 valent PnC

| Type | Infants (post 3 doses PnC) | | Elderly (post 1 dose PnC) | | Elderly (post 1 dose 23vPs) | |
|---|---|---|---|---|---|---|
| | ELISA | OPA | ELISA | OPA | ELISA | OPA |
| 4 | 3.29 | 1571 | 3.27 | 1504 | 1.4 | 669.9 |
| 6B | 5.18 | 1888 | 8.02 | 1351.2 | 4.56 | 809.2 |
| 9V | 1.88 | 3551 | 9.82 | 2914.6 | 3.63 | 984.6 |

TABLE 14-continued

Pneumococcal Antibody Levels in Elderly Subjects immunized with one dose of 7 Valent PnC or 23 valent Ps vs. Infants Immunized with 3 doses of 7 valent PnC

| Type | Infants (post 3 doses PnC) | | Elderly (post 1 dose PnC) | | Elderly (post 1 dose 23vPs) | |
|---|---|---|---|---|---|---|
| | ELISA | OPA | ELISA | OPA | ELISA | OPA |
| 14 | 7.13 | 3017 | 17.5 | 2165 | 8.5 | 974.5 |
| 18C | 2.88 | 1559 | 12.97 | 1317.5 | 6.82 | 464.6 |
| 19F | 4.17 | 203 | 5.5 | 182.2 | 4.43 | 202.7 |
| 23F | 2.16 | 4845 | 12.4 | 1309.3 | 3.97 | 302.4 |

One skilled in the art will readily ascertain the essential characteristics of the invention, and understand that the foregoing description and examples are illustrative of practicing the provided invention. Those skilled in the art will be able to ascertain using no more than routine experimentation, many variations of the detail presented herein may be made to the specific embodiments of the invention described herein without departing from the spirit and scope of the present invention.

Patents, patent applications, publications, and the like are cited throughout the application. The disclosures of each of these documents are incorporated herein by reference in their entirety.

What is claimed is:

1. A method of eliciting an immunoprotective antibody response to a capsular polysaccharide of *Streptococcus pneumoniae* in an older subject who is 65 years or over in age, comprising administering to a first older subject who has never previously received a 23-valent unconjugated pneumococcal polysaccharide vaccine or a 7-valent pneumococcal polysaccharide conjugate vaccine an immunogenic amount of a pneumococcal polysaccharide conjugate vaccine comprising polysaccharides of serotypes 4, 6B, 9V, 14, 18C, 19F, and 23F conjugated to $CRM_{197}$, wherein the antibody response for serotypes 4, 6B, 9V, 14, 18C, and 23F is higher relative to a second older subject who received a 23-valent unconjugated pneumococcal polysaccharide vaccine.

2. The method of claim 1, further comprising administering at least one additional vaccine dose to the first subject, wherein the at least one additional vaccine dose is selected from the group consisting of a pneumococcal polysaccharide conjugate vaccine composition and an unconjugated pneumococcal polysaccharide vaccine composition.

3. The method of claim 2, wherein the at least one additional vaccine dose is administered at least twelve months following the initial vaccine administration.

4. The method of claim 2, wherein the at least one additional vaccine dose comprises a pneumococcal polysaccharide conjugate vaccine.

5. The method of claim 2, wherein the at least one additional vaccine dose comprises an unconjugated pneumococcal polysaccharide vaccine composition.

6. The method of claim 1, wherein the conjugated vaccine is selected from the group consisting of a 7-valent, 9-valent, 10-valent, 11-valent and 13-valent vaccine.

7. The method of claim 5, wherein the unconjugated pneumococcal polysaccharide vaccine is a 23-valent pneumococcal polysaccharide vaccine.

8. The method of claim 1, wherein the conjugate vaccine comprises polysaccharides of serotypes 1, 4, 5, 6B, 7F, 9V, 14, 18C, 19F, and 23F.

9. The method of claim 1, wherein the conjugated vaccine comprises polysaccharides of serotypes 1, 3, 4, 5, 6B, 7F, 9V, 14, 18C, 19F, and 23F.

10. The method of claim 1, wherein the conjugated vaccine comprises polysaccharides of serotypes 1, 3, 4, 5, 6A, 6B, 7F, 9A, 9V, 14, 18C, 19F, and 23F.

11. The method of claim 7, wherein the unconjugated vaccine comprises polysaccharides of serotypes 1, 2, 3, 4, 5, 6B, 7F, 8, 9N, 9V, 10A, 11A, 12F, 14, 15B, 17F, 18C, 19A, 19F, 20, 22F, 23F, and 33F.

12. The method of claim 4, wherein the conjugate vaccine comprises polysaccharides of serotypes 4, 6B, 9V, 14, 18C, 19F, and 23F.

13. The method of claim 4, wherein the conjugate vaccine comprises polysaccharides of serotypes 1, 4, 5, 6B, 7F, 9V, 14, 18C, 19F, and 23F.

14. The method of claim 4, wherein the conjugate vaccine comprises polysaccharides of serotypes 1, 3, 4, 5, 6B, 7F, 9V, 14, 18C, 19F, and 23F.

15. The method of claim 4, wherein the conjugate vaccine comprises polysaccharides of serotypes 1, 3, 4, 5, 6A, 6B, 7F, 9A, 9V, 14, 18C, 19F, and 23F.

16. The method of claim 4, wherein the polysaccharides are conjugated to a polypeptide carrier.

17. The method of claim 16, wherein the polypeptide carrier is selected from the group consisting of the meningococcal outer membrane protein complex, $CRM_{197}$, diphtheria toxoid, tetanus toxoid, and protein D from *H. influenzae*.

18. The method of claim 12, wherein the conjugate vaccine comprises polysaccharides of serotypes 4, 6B, 9V, 14, 18C, 19F, and 23F conjugated to $CRM_{197}$.

19. A method of eliciting an immunoprotective antibody response to a capsular polysaccharide of *Streptococcus pneumoniae* in an older subject who is 65 years or over in age, comprising administering to a first older subject who has never previously received a 23-valent unconjugated pneumococcal polysaccharide vaccine or a 7-valent pneumococcal polysaccharide conjugate vaccine an immunogenic amount of a pneumococcal polysaccharide conjugate vaccine; and
administering to the first older subject a second dose comprising an immunogenic amount of an unconjugated pneumococcal polysaccharide vaccine,
wherein the second dose is administered at least twelve months following the first dose, wherein the pneumococcal polysaccharide conjugate vaccine comprises polysaccharides of serotypes 4, 6B, 9V, 14, 18C, 19F, and 23F conjugated to $CRM_{197}$, and wherein the antibody response for serotypes 6B, 9V, 14, 18C, 19F, and 23F after the second dose is higher relative to a second older subject who received a single dose of a 23-valent unconjugated pneumococcal polysaccharide vaccine.

20. The method of claim 19, further comprising administering at least one additional vaccine dose, wherein the at least one additional vaccine dose is selected from the group consisting of a pneumococcal polysaccharide conjugate vaccine composition and an unconjugated pneumococcal polysaccharide vaccine composition.

21. The method of claim 20, wherein the at least one additional vaccine dose is administered at least one year after the prior dose.

22. The method of claim 20, wherein the at least one additional vaccine dose comprises a pneumococcal polysaccharide conjugate vaccine.

23. The method of claim 20, wherein the at least one additional vaccine dose comprises an unconjugated pneumococcal polysaccharide vaccine composition.

24. The method of claim 19, wherein the conjugated vaccine is selected from the group consisting of a 7-valent, 9-valent, 10-valent, 11-valent and 13-valent vaccine.

25. The method of claim 19, wherein the unconjugated polysaccharide vaccine is a 23-valent pneumococcal polysaccharide vaccine.

26. The method of claim 19, wherein the conjugated vaccine comprises polysaccharides of serotypes 1, 4, 5, 6B, 7F, 9V, 14, 18C, 19F, and 23F.

27. The method of claim 19, wherein the conjugated vaccine comprises polysaccharides of serotypes 1, 3, 4, 5, 6B, 7F, 9V, 14, 18C, 19F, and 23F.

28. The method of claim 19, wherein the conjugated vaccine comprises polysaccharides of serotypes 1, 3, 4, 5, 6A, 6B, 7F, 9A, 9V, 14, 18C, 19F, and 23F.

29. The method of claim 25, wherein the unconjugated vaccine comprises polysaccharides of serotypes 1, 2, 3, 4, 5, 6B, 7F, 8, 9N, 9V, 10A, 11A, 12F, 14, 15B, 17F, 18C, 19A, 19F, 20, 22F, 23F, and 33F.

30. The method of claim 22, wherein the conjugate vaccine comprises polysaccharides of serotypes 4, 6B, 9V, 14, 18C, 19F, and 23F.

31. The method of claim 22, wherein the conjugate vaccine comprises polysaccharides of serotypes 1, 4, 5, 6B, 7F, 9V, 14, 18C, 19F, and 23F.

32. The method of claim 22, wherein the conjugate vaccine comprises polysaccharides of serotypes 1, 3, 4, 5, 6B, 7F, 9V, 14, 18C, 19F, and 23F.

33. The method of claim 22, wherein the conjugate vaccine comprises polysaccharides of serotypes 1, 3, 4, 5, 6A, 6B, 7F, 9A, 9V, 14, 18C, 19F, and 23F.

34. The method of claim 22, wherein the polysaccharides are conjugated to a polypeptide carrier.

35. The method of claim 34, wherein the polypeptide carrier is selected from the group consisting of the meningococcal outer membrane protein complex, $CRM_{197}$, diphtheria toxoid, tetanus toxoid, and protein D from *H. influenzae*.

36. The method of claim 30, wherein the conjugate vaccine comprises polysaccharides of serotypes 4, 6B, 9V, 14, 18C, 19F, and 23F conjugated to CRM197.

* * * * *